US 10,669,287 B2

(12) United States Patent
Kanai et al.

(10) Patent No.: US 10,669,287 B2
(45) Date of Patent: Jun. 2, 2020

(54) CURCUMIN-BORON COMPLEX AND PHARMACEUTICAL CONTAINING SAME

(71) Applicant: JAPAN SCIENCE AND TECHNOLOGY AGENCY, Kawaguchi-shi (JP)

(72) Inventors: Motomu Kanai, Bunkyo-ku (JP); Yohei Soma, Bunkyo-ku (JP); Jizhi Ni, Bunkyo-ku (JP); Atsuhiko Taniguchi, Hachioji (JP)

(73) Assignee: JAPAN SCIENCE AND TECHNOLOGY AGENCY, Kawaguchi-shi (JP)

( * ) Notice: Subject to any disclaimer, the term of this patent is extended or adjusted under 35 U.S.C. 154(b) by 0 days.

(21) Appl. No.: 16/087,017

(22) PCT Filed: Mar. 21, 2017

(86) PCT No.: PCT/JP2017/011232
§ 371 (c)(1),
(2) Date: Sep. 20, 2018

(87) PCT Pub. No.: WO2017/164172
PCT Pub. Date: Sep. 28, 2017

(65) Prior Publication Data
US 2019/0100537 A1  Apr. 4, 2019

(30) Foreign Application Priority Data
Mar. 22, 2016  (JP) .................. 2016-056615

(51) Int. Cl.
C07F 5/02 (2006.01)
A61P 25/16 (2006.01)
A61P 25/28 (2006.01)
A61P 3/10 (2006.01)
A61K 31/69 (2006.01)

(52) U.S. Cl.
CPC ............. C07F 5/02 (2013.01); A61K 31/69 (2013.01); A61P 3/10 (2018.01); A61P 25/16 (2018.01); A61P 25/28 (2018.01)

(58) Field of Classification Search
CPC .... C07F 5/02; A61P 25/28; A61P 3/10; A61P 25/16; A61K 31/69
USPC ......................................................... 514/64
See application file for complete search history.

(56) References Cited

U.S. PATENT DOCUMENTS

| 5,679,864 A | 10/1997 | Krackov et al. |
| 2017/0197956 A1 | 7/2017 | Kanai et al. |
| 2018/0042948 A1 | 2/2018 | Kanai et al. |

FOREIGN PATENT DOCUMENTS

| EP | 2 857 379 | 4/2015 |
| WO | WO 2010/017094 A2 | 2/2010 |
| WO | WO 2011/014648 A2 | 2/2011 |

(Continued)

OTHER PUBLICATIONS

International Search Report dated Jun. 27, 2017, in PCT/JP2017/011232 filed Mar. 21, 2017.
Abstracts of 136th Annual Meeting of Pharmaceutical Society of Japan, 2016, 29T-pm15 (3 total pages).
Taniguchi, A. et al, "Development of Amyloid-Selective Photooxygenation Catalyst toward Treatment of Amyloid Disease", The 32nd Medicinal Chemistry Symposium Abstracts, 2014, p. 87, 1P-24 (3 total pages) (with English Translation).
Abstracts, 40th Symposium on Progress in Organic Reactions and Syntheses—Applications in the Life Sciences—2014, (4 total pages).
Hou, L., et al., "Methionine 35 Oxidation Reduces Fibril Assembly of the Amyloid Aβ-(1-42) Peptide of Alzheimer's Disease", The Journal of Biological Chemistry, vol. 277, No. 43, 2002 (5 total pages).

(Continued)

Primary Examiner — Kristin A Vajda
(74) Attorney, Agent, or Firm — Oblon, McClelland, Maier & Neustadt, L.L.P.

(57) ABSTRACT

Provided is a compound which is bioapplicable and amyloid-selective, and is useful as an amyloid oxygenation catalyst applicable not only to Aβ peptides but also to other amyloids, and a preventive/therapeutic drug for an amyloid-related disease using the same. A curcumin-boron complex represented by the following formula (1):

(1)

wherein $X^1$ and $X^2$ are identical or different, and each represent a halogenoalkyl group or a halogen atom; $X^3$ represents a bromine atom, an iodine atom, or a selenium atom; $R^1$ and $R^2$ are identical or different, and each represent a hydrogen atom or an optionally substituted alkyl group; $R^3$ and $R^4$ are identical or different, and each represent a hydrogen atom, a halogen atom, an alkoxy group, or an optionally substituted alkyl group, or $R^1$ and $R^3$ or $R^2$ and $R^4$ are optionally taken together to form an optionally substituted alkylene group or alkenylene group; $R^5$ and $R^6$ are identical or different, and each represent a hydrogen atom or an optionally substituted alkyl group; $R^7$ and $R^8$ are identical or different, and each represent a hydrogen atom, a halogen atom, an alkoxy group, or an optionally substituted alkyl group, or $R^5$ and $R^7$ or $R^6$ and $R^8$ are optionally taken together to form an optionally substituted alkylene group or alkenylene group; and m and n each represent an integer of 1 to 3, or a salt thereof.

9 Claims, 14 Drawing Sheets

(56) References Cited

FOREIGN PATENT DOCUMENTS

| | | |
|---|---|---|
| WO | WO 2014/025808 A1 | 2/2014 |
| WO | WO 2015/034996 A1 | 3/2015 |
| WO | WO 2016/010092 A1 | 1/2016 |
| WO | WO 2016/143699 A1 | 9/2016 |

OTHER PUBLICATIONS

Bitan, G., et al., "A Molecular Switch in Amyloid Assembly: Met$^{35}$ and Amyloid β-Protein Oligomerization", J. Am. Chem. Soc., vol. 125, No. 50, 2003, pp. 15359-15365.

Moskovitz, J., et al., "Induction of Methionine-Sulfoxide Reductases Protects Neurons from Amyloid β-Protein Insults in Vitro and in Vivo", Biochemistry, 2011, vol. 50, pp. 10687-10697.

Taniguchi, A., et al., "Attenuation of the Aggregation and Neurotoxicity of Amyloid-β Peptides by Catalytic Photooxygenation", Angewandte Communications, Angewandte Chemie International Edition, 2014, vol. 53, No. 5, pp. 1382-1385.

Z. Sui, et al. "Inhibition of the HIV-1 and HIV-2 proteases by curcumin and curcumin boron complexes", (https://doi.org/10.1016/s0968-0896(00)82152-5), vol. 1, Issue 6, Dec. 1993, pp. 415-422. (Abstract Only).

Office Action in corresponding Indian Application No. 201817035094, dated Sep. 13, 2019. (w/English Translation).

Extended European Search Report(EESR) dated Oct. 2, 2019 for European Patent Application No. 17770214.9.

Simon Wanninger, et al., "Metal complexes of curcumin—synthetic strategies, structures and medicinal applications", Chemical Society Reviews, vol. 44, No. 15, Jan. 1, 2015, pp. 4986-5002.

Hideyuki Okamoto, et al., "Inactivation of myostatin by photooxygenation using catalyst-functionalized peptides", Chemical Communications, Issue 62, Jan. 1, 2019, Retrieved from the Internet: URL: https://pubs.rsc.org/en/content/articlelanding/2019/cc/c9cc04368c#!divAbstract.

Office Action dated Mar. 30, 2020 for Chinese Patent Application No. 201780018865.2 (with machine translation).

Kenji Kamada, et al., "Boron Difluoride Curcuminoid Fluorophores with Enhanced Two-Photon Excited Fluorescence Emission and Versatile Living-Cell Imaging Properties", Chemistry A European Journal—vol. 22, Issue 15, Feb. 25, 2016 (Abstract only).

[Figure 1]
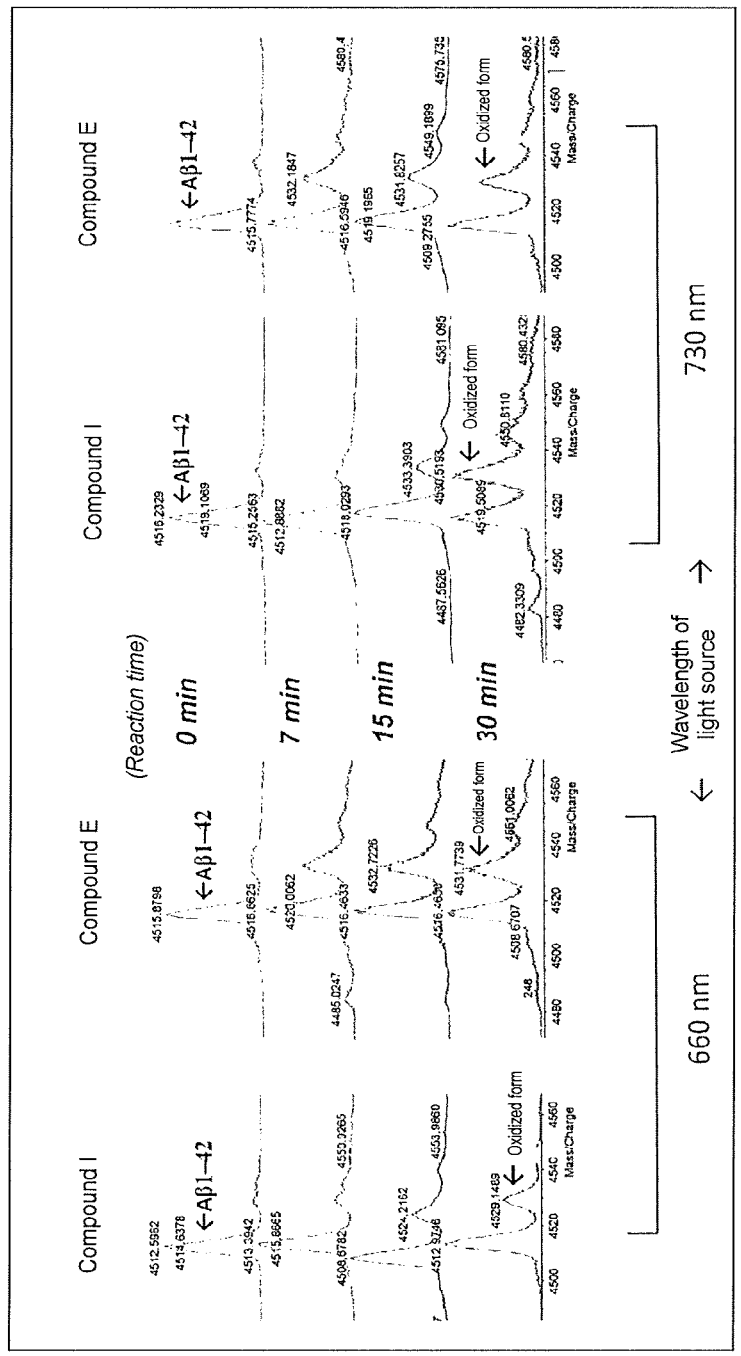

[Figure 2]
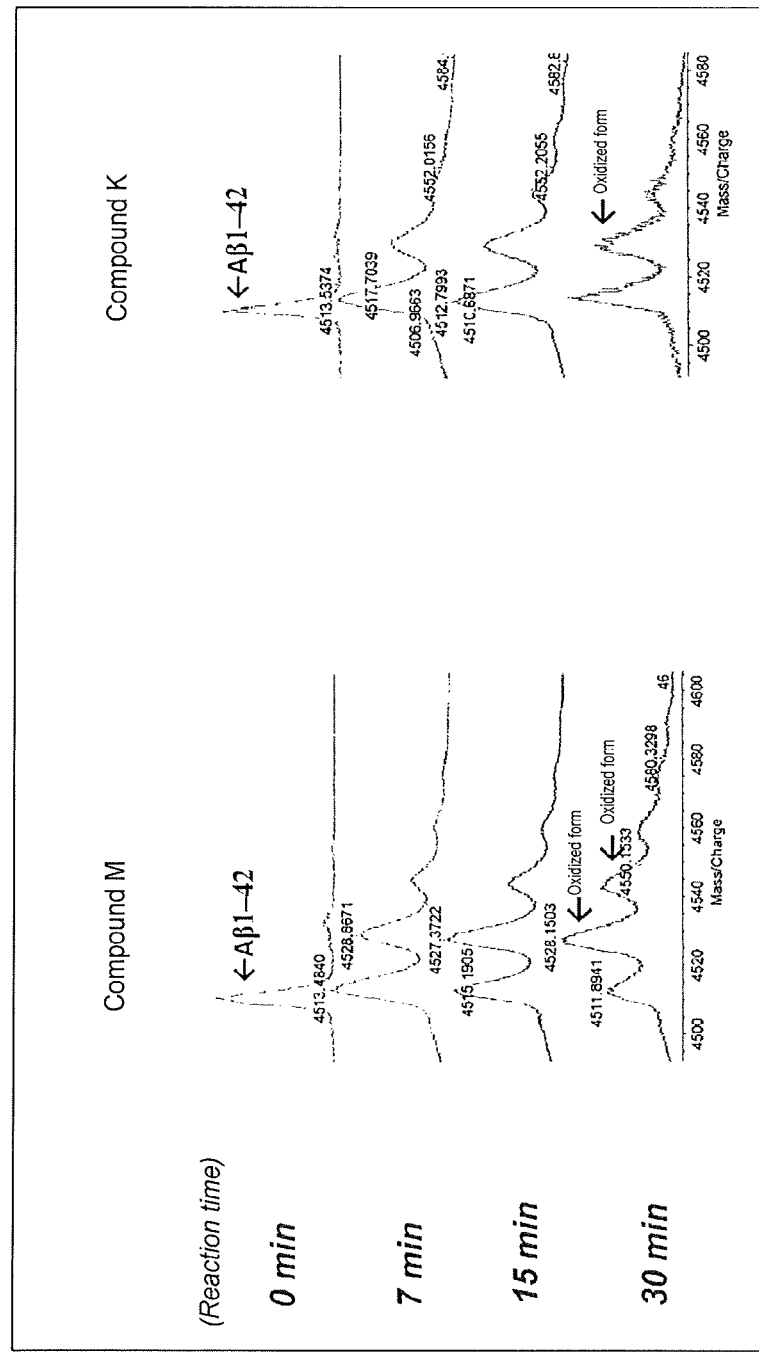

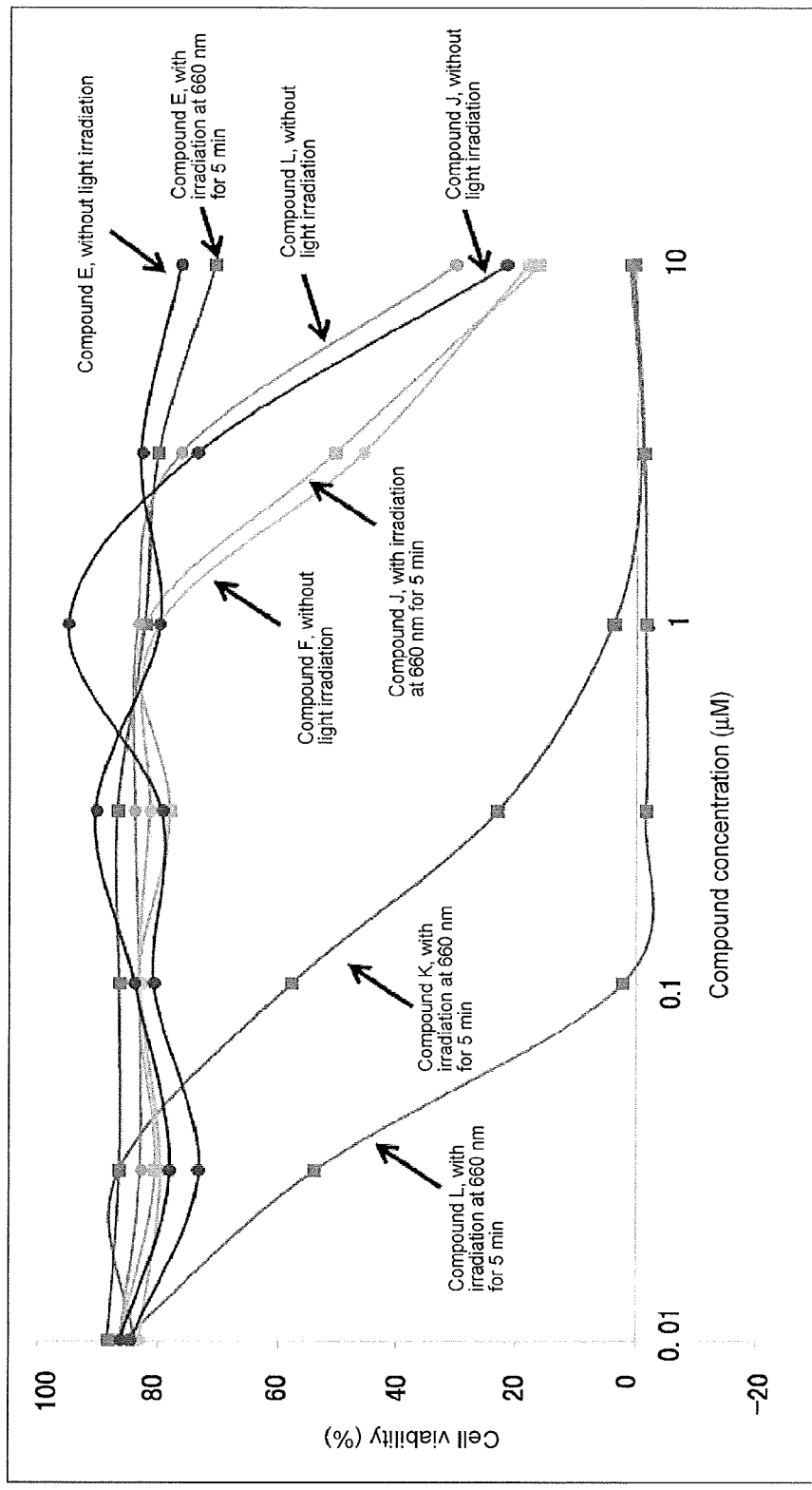
[Figure 3]

[Figure 4]
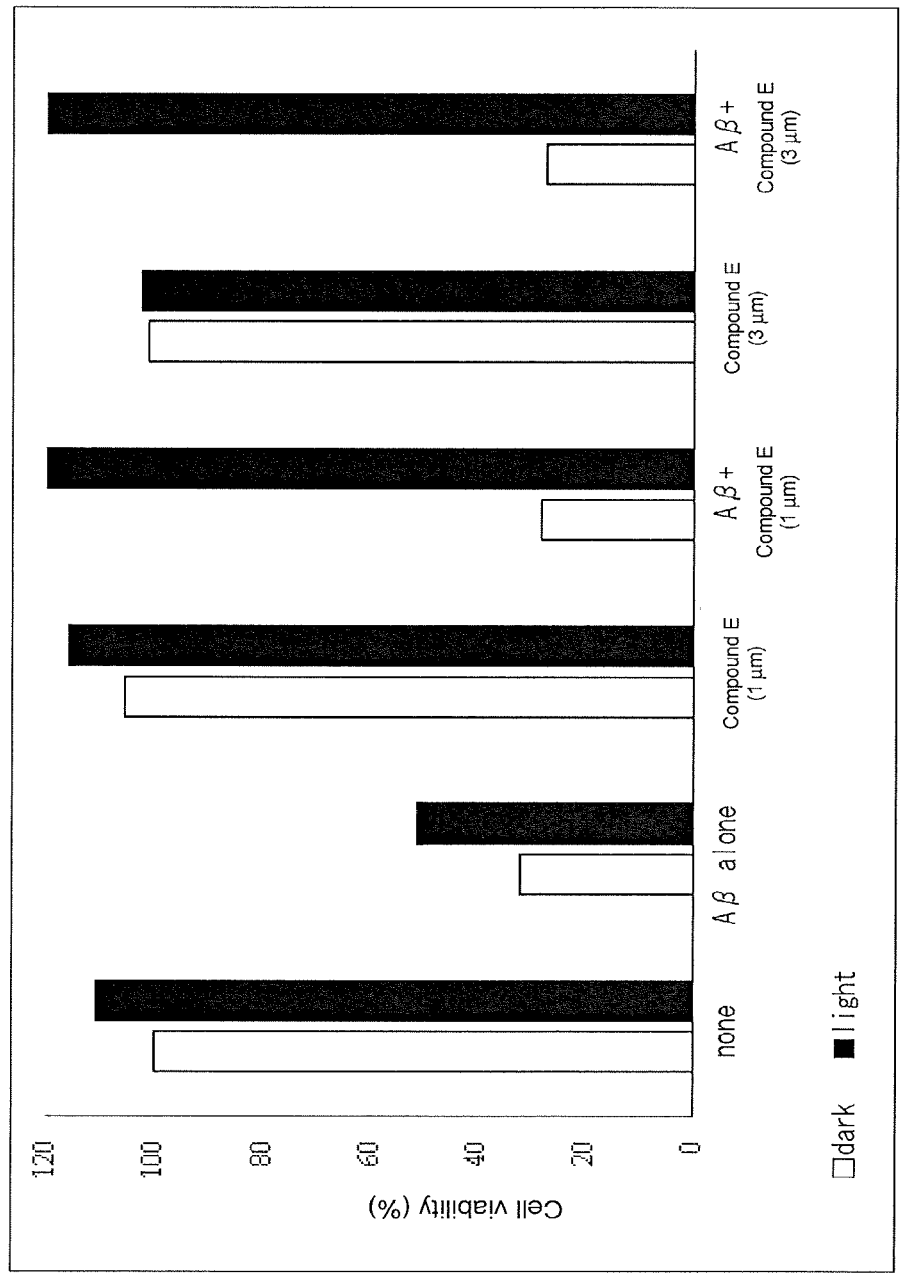

[Figure 5]
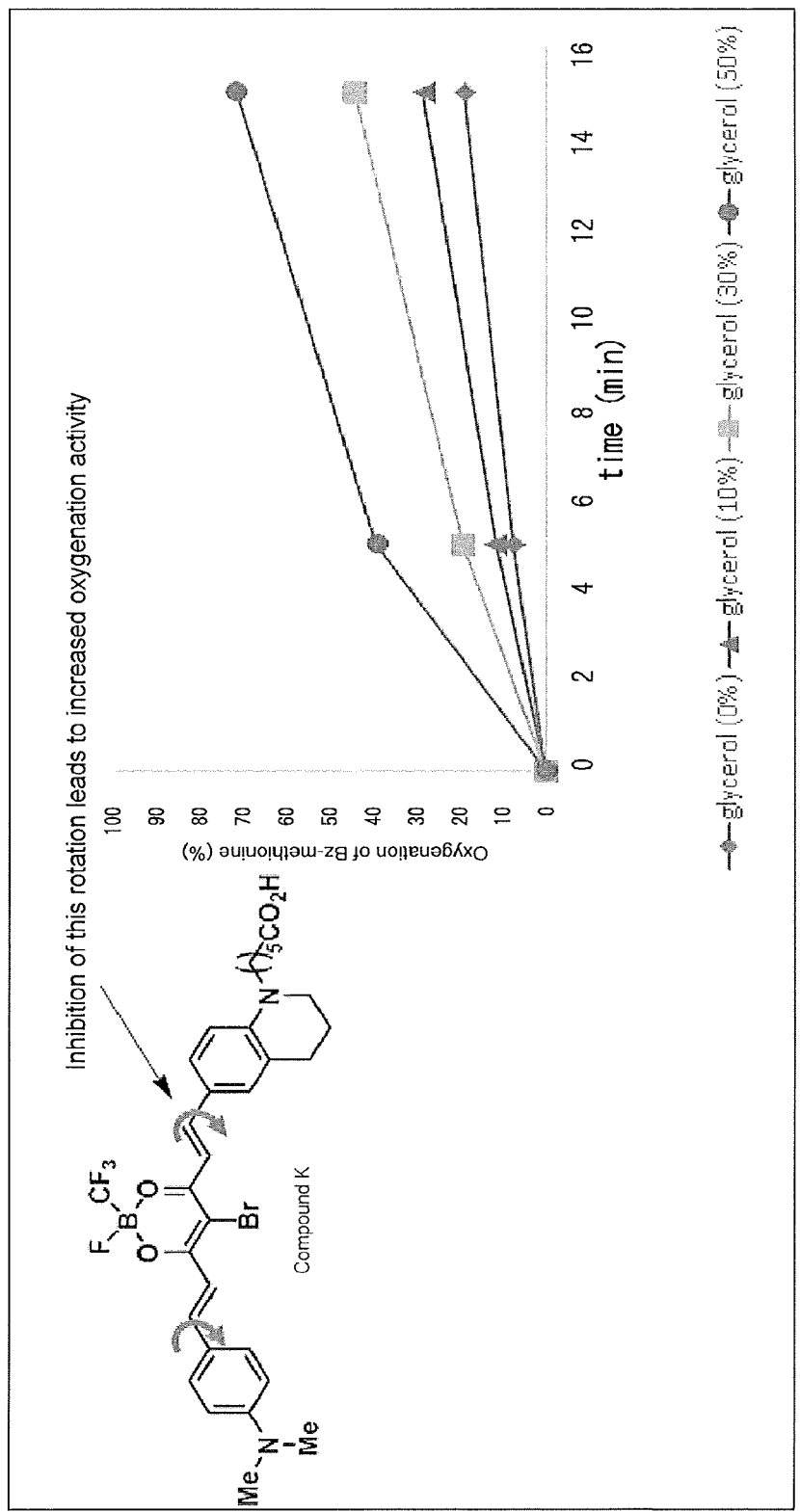

[Figure 6]
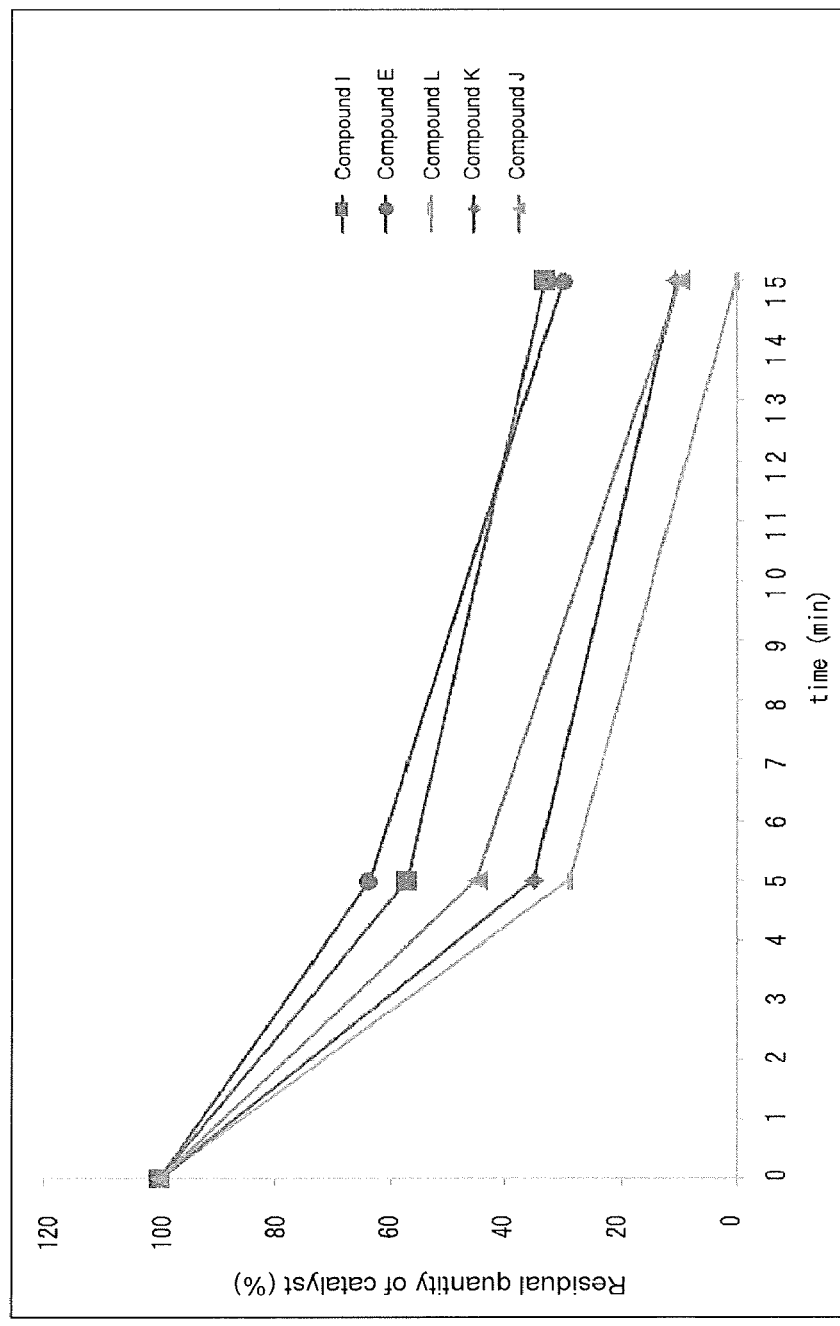

[Figure 7]
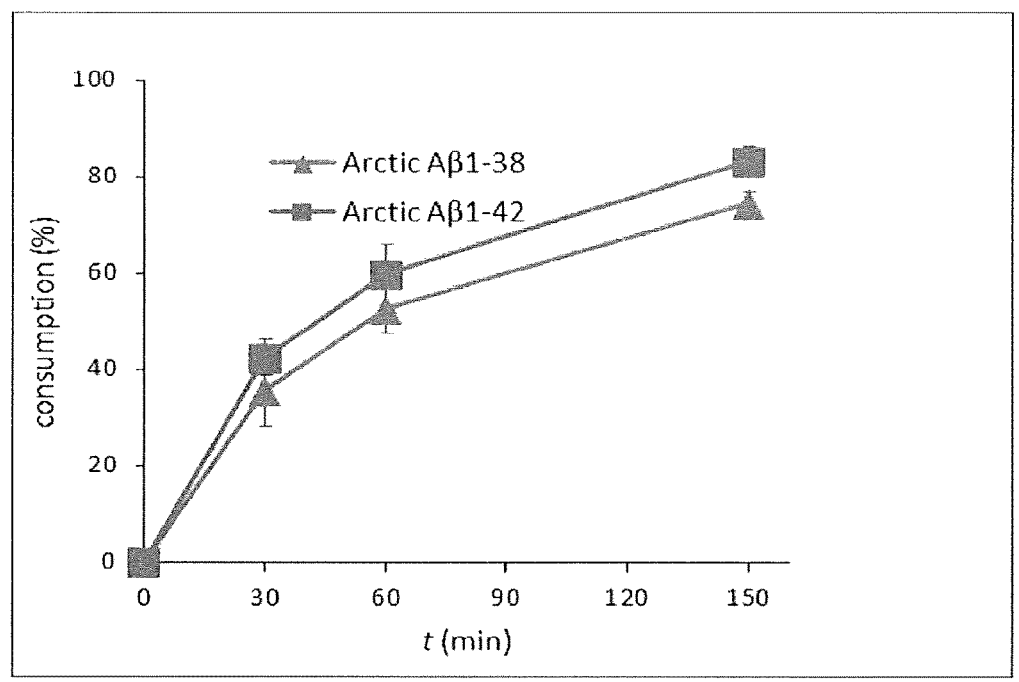

[Figure 8]
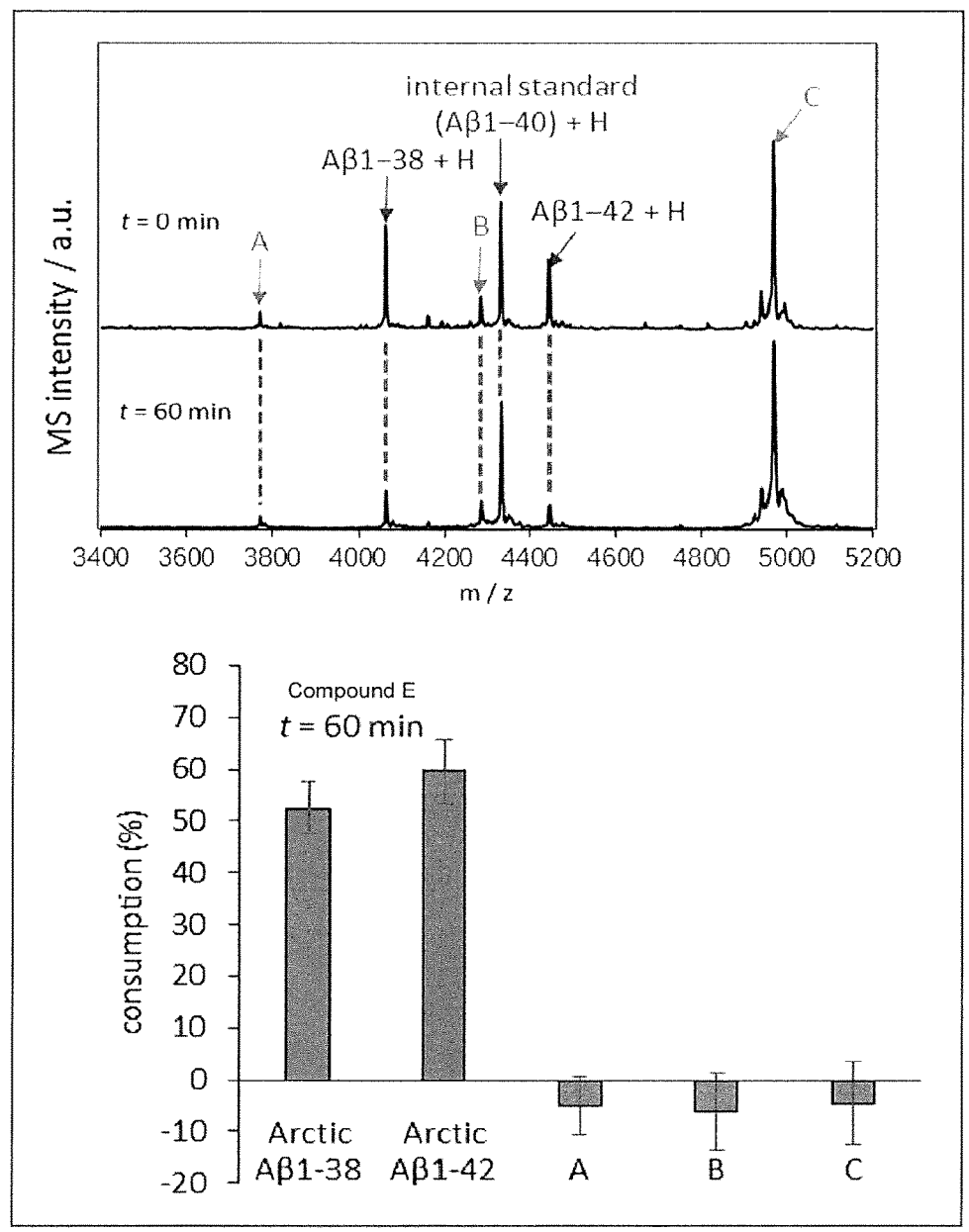

[Figure 9]
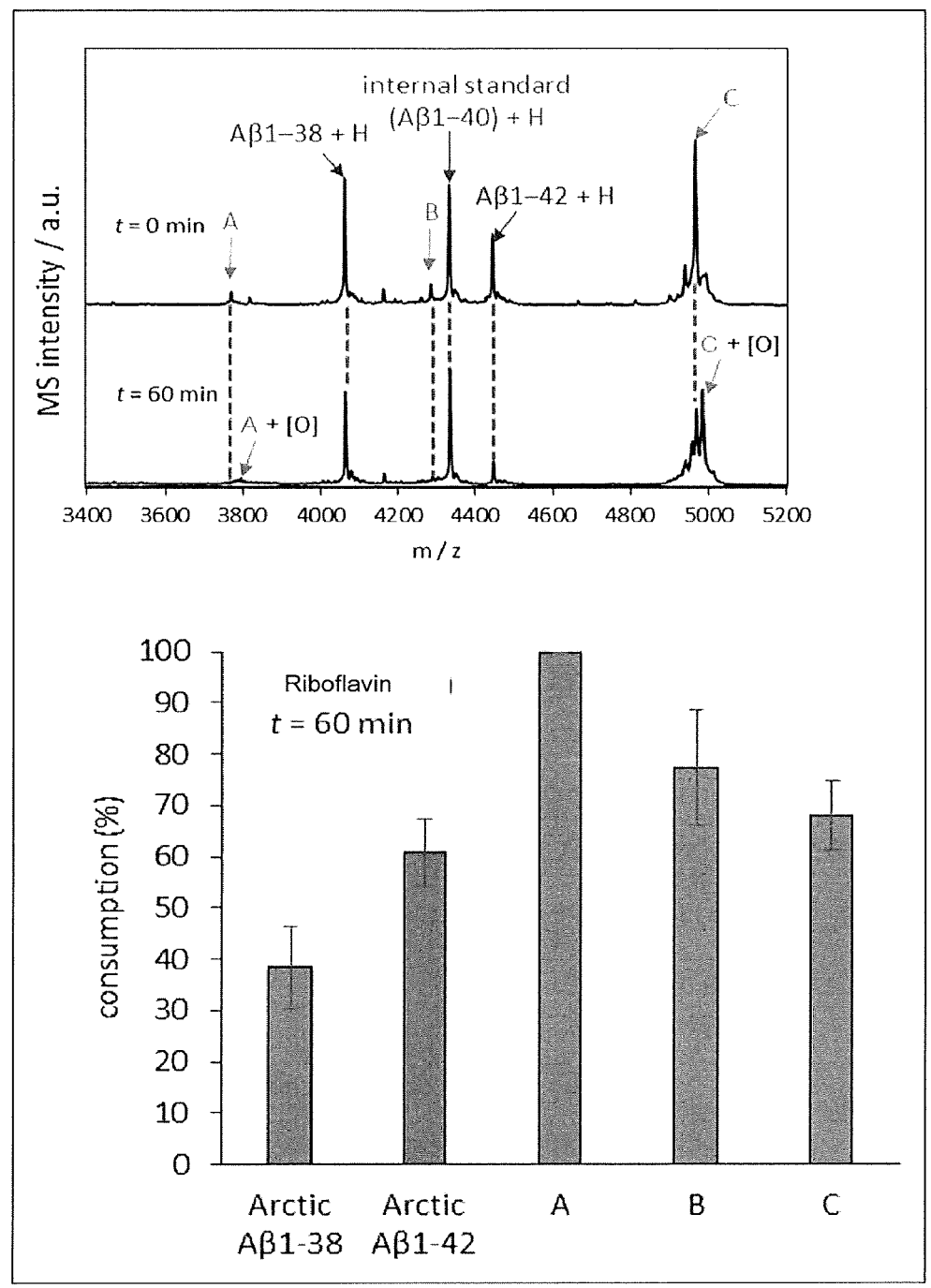

[Figure 10]
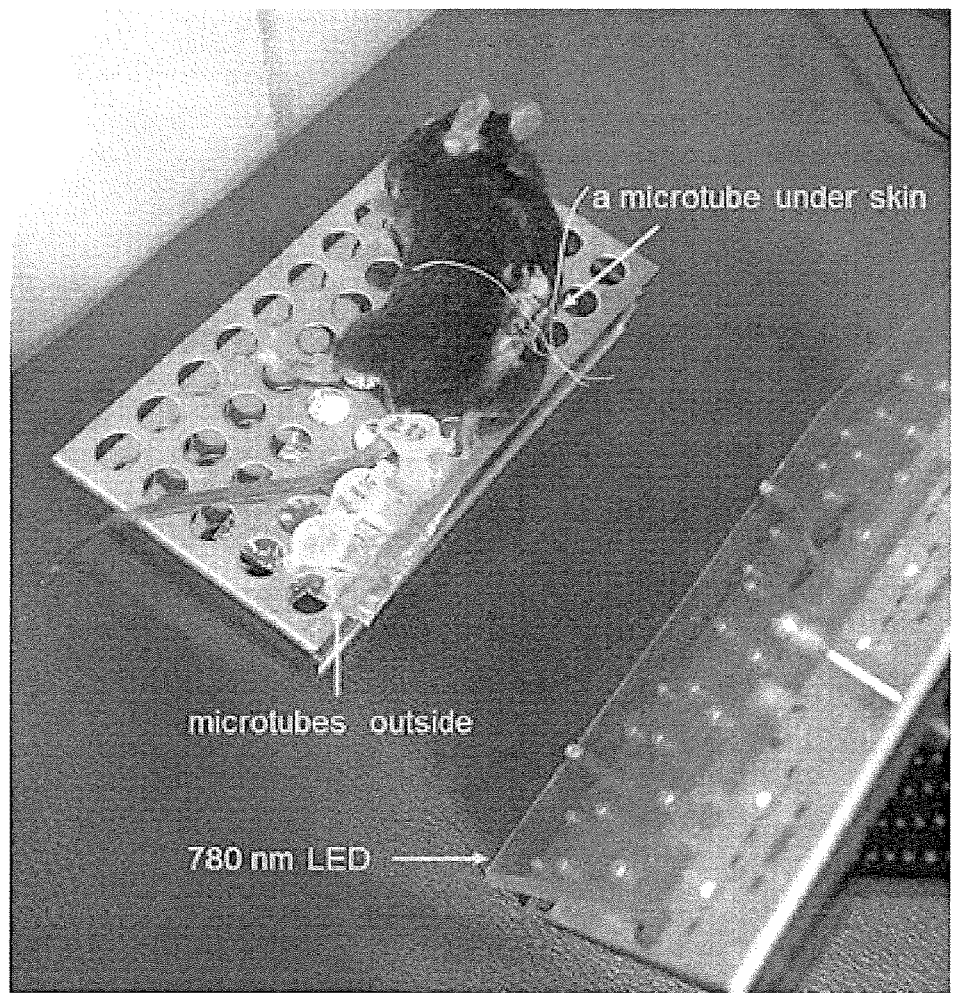

[Figure 11]
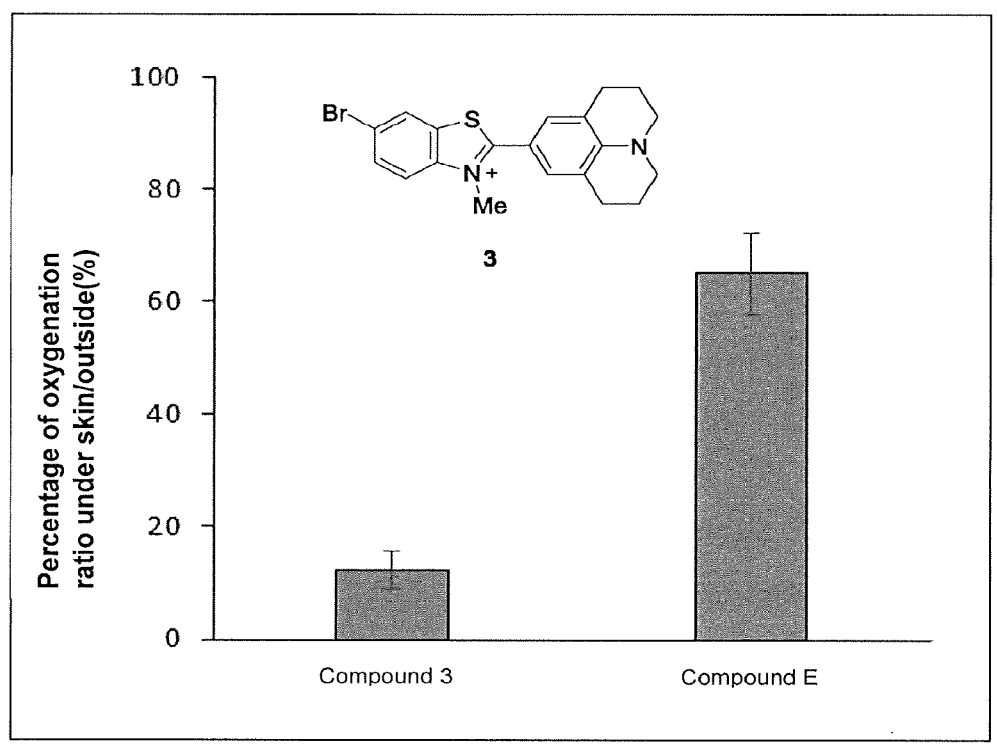

[Figure 12]
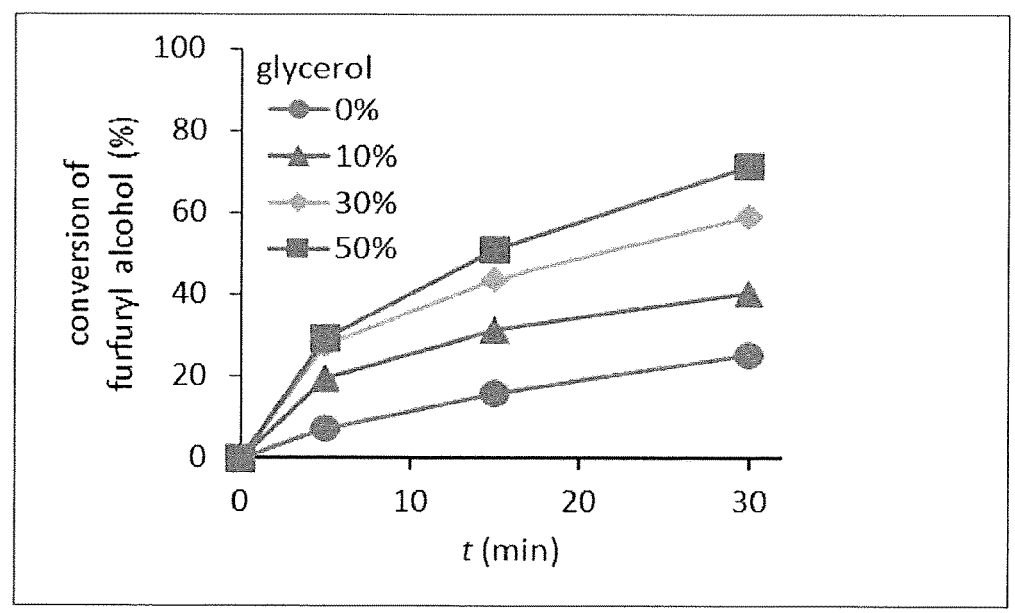

[Figure 13]
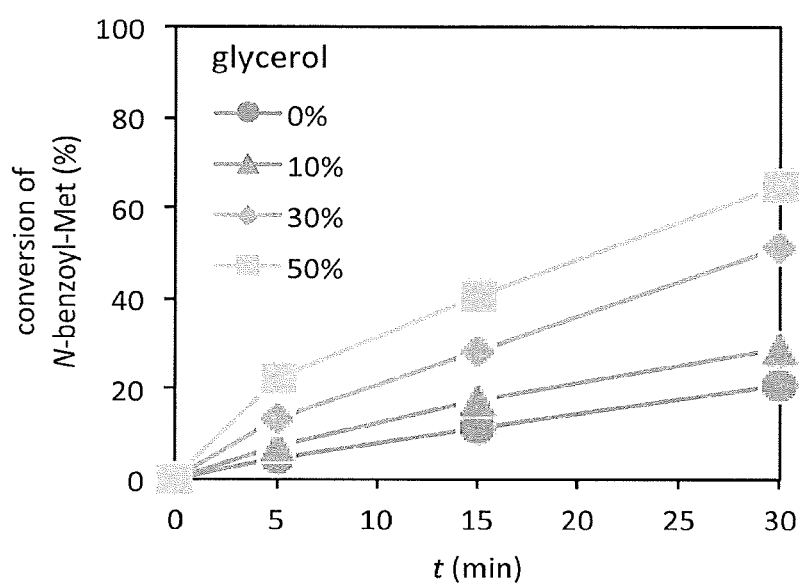

[Figure 14]
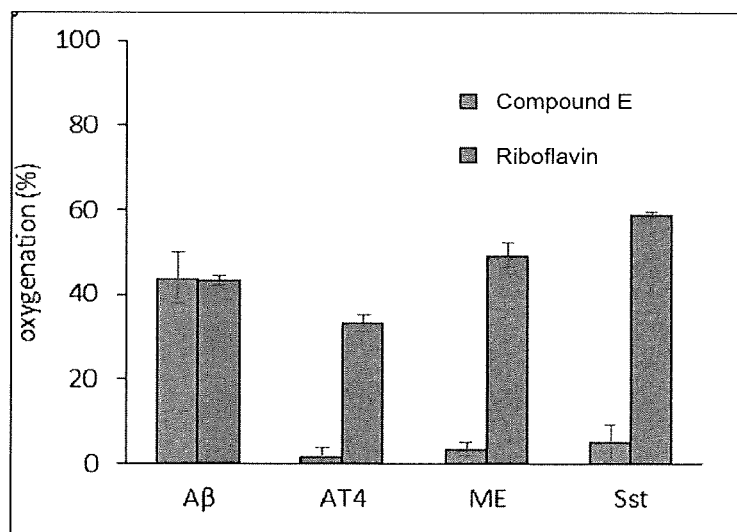

CURCUMIN-BORON COMPLEX AND PHARMACEUTICAL CONTAINING SAME

TECHNICAL FIELD

The present invention relates to a pharmaceutical for preventing or treating various pathogenic amyloid-associated diseases.

BACKGROUND ART

While protein typically forms a specific native structure through folding to play a role in biological functions, it may aggregate into a fiber including many β-sheet structures (amyloid formation) through misfolding. Aggregates (oligomers, protofibrils, fibers) produced in the course of the amyloid formation are known to cause various functional disorders (such diseases are collectively referred to as "amyloid diseases"), and 20 or more proteins have been identified as causal substances for amyloid diseases. Known examples of such amyloid include amyloid β for Alzheimer's disease, tau protein, α-synuclein for Parkinson's disease, amylin for diabetes mellitus, transthyretin for systemic amyloidosis, and huntingtin for Huntington's disease.

With regard to development strategy for therapeutic drugs targeting these pathogenic amyloids, known examples for the case of amyloid β (abbreviated as "Aβ"), which is a causal amyloid for Alzheimer's disease, include an inhibitor for an enzyme which produces Aβ from a precursor protein, an accelerator for an Aβ-degrading enzyme, immunotherapy, and an inhibitor for Aβ aggregation.

Previous studies on Aβ have reported that a small quantity of an Met-oxygenated form of Aβ peptide (an oxygenated form with the sulfur atom of an Met residue in Aβ peptide oxygenated (O)) remains in the living body, and that the Met-oxygenated form has lower aggregability than the Aβ peptide (Non Patent Literatures 1 to 3). From these viewpoints, the present inventors have reported that oxygenation of Aβ peptide by using a flavin photocatalyst having an Aβ-binding site represented by a formula (a) provides an oxygenated form of Aβ peptide, and the oxygenated form of Aβ peptide suppresses the aggregation of Aβ (Non Patent Literature 4).

CITATION LIST

Non Patent Literature

[Non Patent Literature 1] Hou, L. et al. J. Biol. Chem., 2002, Vol. 277, No. 43, p 40173-40176
[Non Patent Literature 2] Bitan, G. et al. J. Am. Chem. Soc., 2003, Vol. 125, No. 50, p 15359-15365
[Non Patent Literature 3] Moskovitz, J. et al. Biochemistrym, 2011, 50, p 10687-10697
[Non Patent Literature 4] A. Taniguchi et al. Angew. Chem. Int. Ed., 2014, 53, 1382-1385

SUMMARY OF INVENTION

Problem to be Solved by the Invention

Since the flavin photocatalyst used in Non Patent Literature 4 has oxygenation activity even in the absence of Aβ, however, the flavin photocatalyst may react in a non-specific manner in vivo, and is poor in bioapplicability, although it is applicable in vitro. In addition, the flavin photocatalyst is applicable only to Aβ peptides.

Accordingly, an object of the present invention is to provide a compound which is bioapplicable and amyloid-selective, and is useful as an amyloid oxygenation catalyst applicable not only to Aβ peptides but also to other amyloids, and a preventive/therapeutic drug for an amyloid-related disease using the same.

Means for Solving the Problem

Then, the present inventors widely examined to develop a catalyst which has selective oxygenation activity for amyloids and is bioapplicable, and found that a curcumin-boron complex represented by a formula (1) below and characterized in that $X^3$ is a bromine atom, an iodine atom, or a selenium atom exhibits high oxygenation activity for Aβ peptides and other amyloids through light irradiation at a long wavelength, with particularly high oxygenation activity to highly toxic Aβ peptide aggregates and no oxygenation activity for peptides other than amyloids, and has high stability in water and against light irradiation, and thus is useful as a biocatalyst to form an oxygenated form of amyloid having no aggregability. On the basis of the finding, the present inventors completed the present invention.

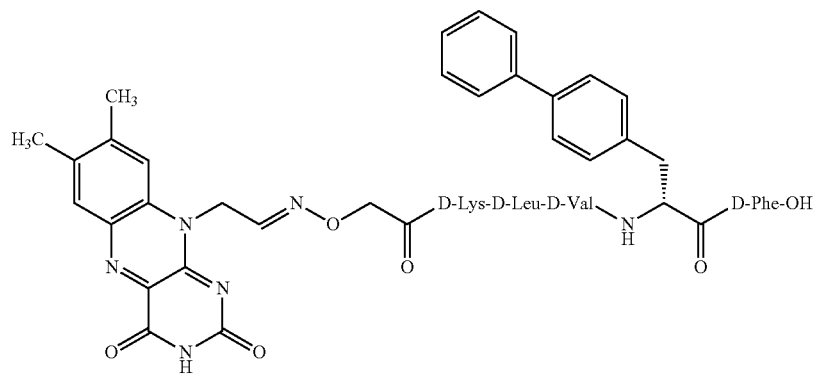

(a)

Specifically, the present invention provides the following [1] to [11].

A curcumin-boron complex represented by the following formula (1):

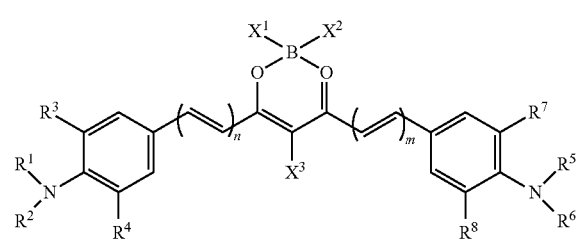

wherein $X^1$ and $X^2$ are identical or different, and each represent a halogenoalkyl group or a halogen atom;

$X^3$ represents a bromine atom, an iodine atom, or a selenium atom;

$R^1$ and $R^2$ are identical or different, and each represent a hydrogen atom or an optionally substituted alkyl group;

$R^3$ and $R^4$ are identical or different, and each represent a hydrogen atom, a halogen atom, an alkoxy group, or an optionally substituted alkyl group, or $R^1$ and $R^3$ or $R^2$ and $R^4$ are optionally taken together to form an optionally substituted alkylene group or alkenylene group;

$R^5$ and $R^6$ are identical or different, and each represent a hydrogen atom or an optionally substituted alkyl group;

$R^7$ and $R^8$ are identical or different, and each represent a hydrogen atom, a halogen atom, an alkoxy group, or an optionally substituted alkyl group, or $R^5$ and $R^7$ or $R^6$ and $R^8$ are optionally taken together to form an optionally substituted alkylene group or alkenylene group; and m and n each represent an integer of 1 to 3, or a salt thereof.

[2] The curcumin-boron complex or salt thereof according to [1], wherein $X^1$ is a halogenoalkyl group, and $X^2$ is a halogen atom.

[3] The curcumin-boron complex or salt thereof according to [1] or [2], wherein m and n are each 1.

[4] The curcumin-boron complex or salt thereof according to any one of [1] to [3], wherein the optionally substituted alkyl group represented by any of $R^1$, $R^2$, $R^3$, $R^4$, $R^5$, $R^6$, $R^7$, and $R^8$ is an alkyl group optionally having one or more substituents selected from the group consisting of a carboxy group, a sulfonic acid group, a hydroxy group, an amino group, —CO—, —CONH—, and a triazole group.

[5] The curcumin-boron complex or salt thereof according to any one of [1] to [4], wherein the alkylene group or alkenylene group formed by $R^1$ and $R^3$, $R^2$ and $R^4$, $R^5$ and $R^7$, or $R^6$ and $R^8$ taken together has two or three carbon atoms.

[6] A pharmaceutical comprising the curcumin-boron complex or salt thereof according to any one of [1] to [5] as an active ingredient.

[7] The pharmaceutical according to [6], being a preventive or therapeutic drug for a pathogenic amyloid-related disease.

[8] A pharmaceutical composition comprising the curcumin-boron complex or salt thereof according to any one of [1] to [5] and a pharmaceutically acceptable carrier.

[9] Use of the curcumin-boron complex or salt thereof according to any one of [1] to [5] for production of a preventive or therapeutic drug for a pathogenic amyloid-associated disease.

[10] The curcumin-boron complex or salt thereof according to any one of [1] to [5] for preventing or treating a pathogenic amyloid-associated disease.

[11] A method for preventing or treating a pathogenic amyloid-related disease, the method comprising administering an effective amount of the curcumin-boron complex or salt thereof according to any one of [1] to [5].

Effects of the Invention

The curcumin-boron complex (1) according to the present invention exhibits high catalytic activity to oxygenate pathogenic amyloids including Aβ peptides through light irradiation at a long wavelength and oxygenates amyloids in the living body to suppress the aggregation of amyloids, with particularly high oxygenation activity for aggregated Aβ peptide and no oxygenation activity for peptides other than amyloids, and has high stability in water and under light irradiation, and thus is useful as a preventive/therapeutic drug for a pathogenic amyloid-associated disease. In the present specification, the term "oxygenation" particularly refers to a reaction to bond an oxygen atom among reactions of oxidation.

BRIEF DESCRIPTION OF DRAWINGS

FIG. 1 shows Aβ peptide oxygenation activities.
FIG. 2 shows the Aβ peptide oxygenation activities of inventive compounds.
FIG. 3 shows the cytotoxicities of inventive compounds under light irradiation.
FIG. 4 shows the action of an inventive compound on cells through selective oxygenation of $Aβ_{1-42}$.
FIG. 5 shows the oxygenation activity of an inventive compound for benzoylmethionine.
FIG. 6 shows the stabilities of inventive compounds under light irradiation.
FIG. 7 shows the oxygenation activity of an inventive compound for Aβ peptides.
FIG. 8 shows the oxygenation activity of an inventive compound for Aβ peptides and non-target molecules.
FIG. 9 shows the oxygenation activity of a reference compound for Aβ peptides and non-target molecules.
FIG. 10 is a photograph showing the situation of an experiment.
FIG. 11 shows ratios of oxygenation of an Aβ peptide for a group with irradiation under the mouse skin to that for a control group (irradiation outside of the mouse body).
FIG. 12 shows the oxygenation activity of an inventive compound for furfuryl alcohol.
FIG. 13 shows the oxygenation activity of an inventive compound for N-benzoyl-Met.
FIG. 14 shows the selectivity of an inventive compound with respect to oxygenation for Aβ peptide.

DESCRIPTION OF EMBODIMENTS

In the formula (1), $X^1$ and $X^2$ are identical or different, and each represents a halogenoalkyl group or a halogen atom. The halogenoalkyl group is preferably a linear or branched halogeno $C_1$-$C_6$ alkyl group, and more preferably a linear or branched halogeno $C_1$-$C_4$ alkyl group. Specific examples of the halogenoalkyl group include perfluoro $C_1$-$C_6$ alkyl groups such as a trifluoromethyl group and a pentafluoroethyl group, and perfluoro $C_1$-$C_4$ alkyl groups are more preferred. Examples of the halogen atom include a fluorine atom, a chlorine atom, a bromine atom, and an iodine atom.

Although $X^1$ and $X^2$ may be simultaneously halogen atoms or halogenoalkyl groups, it is preferable that $X^1$ be a halogenoalkyl group and $X^2$ be a halogen atom, it is more preferable that $X^1$ be a perfluoro $C_1$-$C_6$ alkyl group and $X^2$ be a fluorine atom, and it is even more preferable that $X^1$ be a trifluoromethyl group or pentafluoroethyl group and $X^1$ be a fluorine atom, from the viewpoint of the selectivity of oxygenation activity for amyloids.

$X^3$ represents a bromine atom, an iodine atom, or a selenium atom. The configuration such that $X^3$ is any of these heavy atoms provides high oxygenation activity for amyloids.

$R^1$ and $R^2$ are identical or different, and each represents a hydrogen atom or an optionally substituted alkyl group. $R^3$ and $R^4$ are identical or different, and each represents a hydrogen atom, a halogen atom, an alkoxy group, or an optionally substituted alkyl group, or $R^1$ and $R^3$ or $R^2$ and $R^4$ are optionally taken together to form an optionally substituted alkylene group or alkenylene group. $R^5$ and $R^6$ are identical or different, and each represent a hydrogen atom or an optionally substituted alkyl group. $R^7$ and $R^8$ are identical or different, and each represent a hydrogen atom, a halogen atom, an alkoxy group, or an optionally substituted alkyl group, or $R^5$ and $R^7$ or $R^6$ and $R^8$ are optionally taken together to form an optionally substituted alkylene group or alkenylene group.

The alkyl group represented by any of $R^1$ to $R^8$ is preferably a linear or branched $C_1$-$C_6$ alkyl group, and more preferably a linear or branched $C_1$-$C_4$ alkyl group. Examples of the alkyl group include a methyl group, an ethyl group, an n-propyl group, an isopropyl group, an n-butyl group, an isobutyl group, and a tert-butyl group. Preferred as an optional substituent of these alkyl groups are one to three selected from the group consisting of a carboxy group, a sulfonic acid group, a hydroxy group, an amino group, —CO—, —CONH—, and a triazole group. Among them, a carboxy group, a sulfonic acid group, a hydroxy group, and an amino group are preferred for higher water solubility.

Examples of a preferred substituent include —$(CH_2)_l$—$(Y)_O$—$(CH_2)_p$—Z. Here, Y represents —CO—, —CONH—, or a triazole ring. o represents a number of 0 or 1. Examples of the triazole ring include a 1,2,3-triazol-1,4-diyl group and a 1,2,4-triazol-1,3-diyl group.

l and p are identical or different, and each represent an integer of 1 to 6. l is preferably an integer of 1 to 6, and more preferably an integer of 1 to 4. p is preferably an integer of 1 to 6, and more preferably an integer of 1 to 4.

Z represents a hydroxy group, an amino group, a carboxyl group (—COOH), or a sulfonic acid group (—$SO_3H$). The alkoxy group represented by any of $R^3$, $R^4$, $R^7$, and $R^8$ is preferably a linear or branched $C_1$-$C_6$ alkoxy group, and more preferably a $C_1$-$C_4$ alkoxy group. Specific examples thereof include a methoxy group, an ethoxy group, and a propyloxy group. Examples of the halogen atom include a chlorine atom, a bromine atom, an iodine atom, and a fluorine atom.

The alkylene group formed by $R^1$ and $R^3$, $R^2$ and $R^4$, $R^5$ and $R^7$, or $R^6$ and $R^8$ taken together is preferably a $C_2$-$C_4$ alkylene group, and examples thereof include an ethylene group, a trimethylene group, and a tetramethylene group. Examples of the alkenylene group include a vinylene group and a propenylene group.

Examples of a ring structure formed by these groups taken together include the followings.

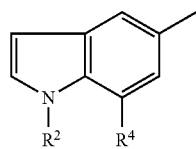
(a)

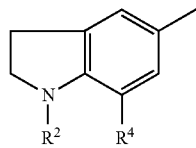
(b)

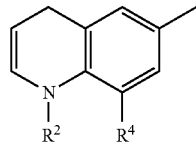
(c)

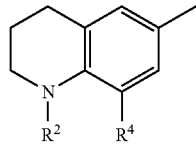
(d)

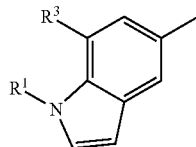
(e)

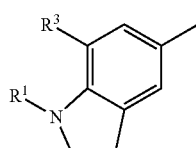
(f)

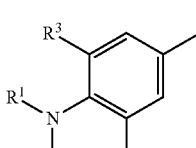
(g)

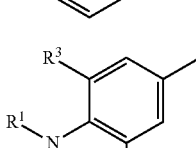
(h)

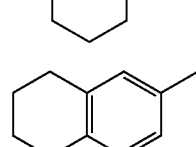
(i)

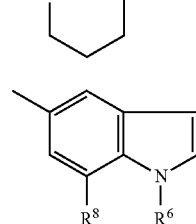
(j)

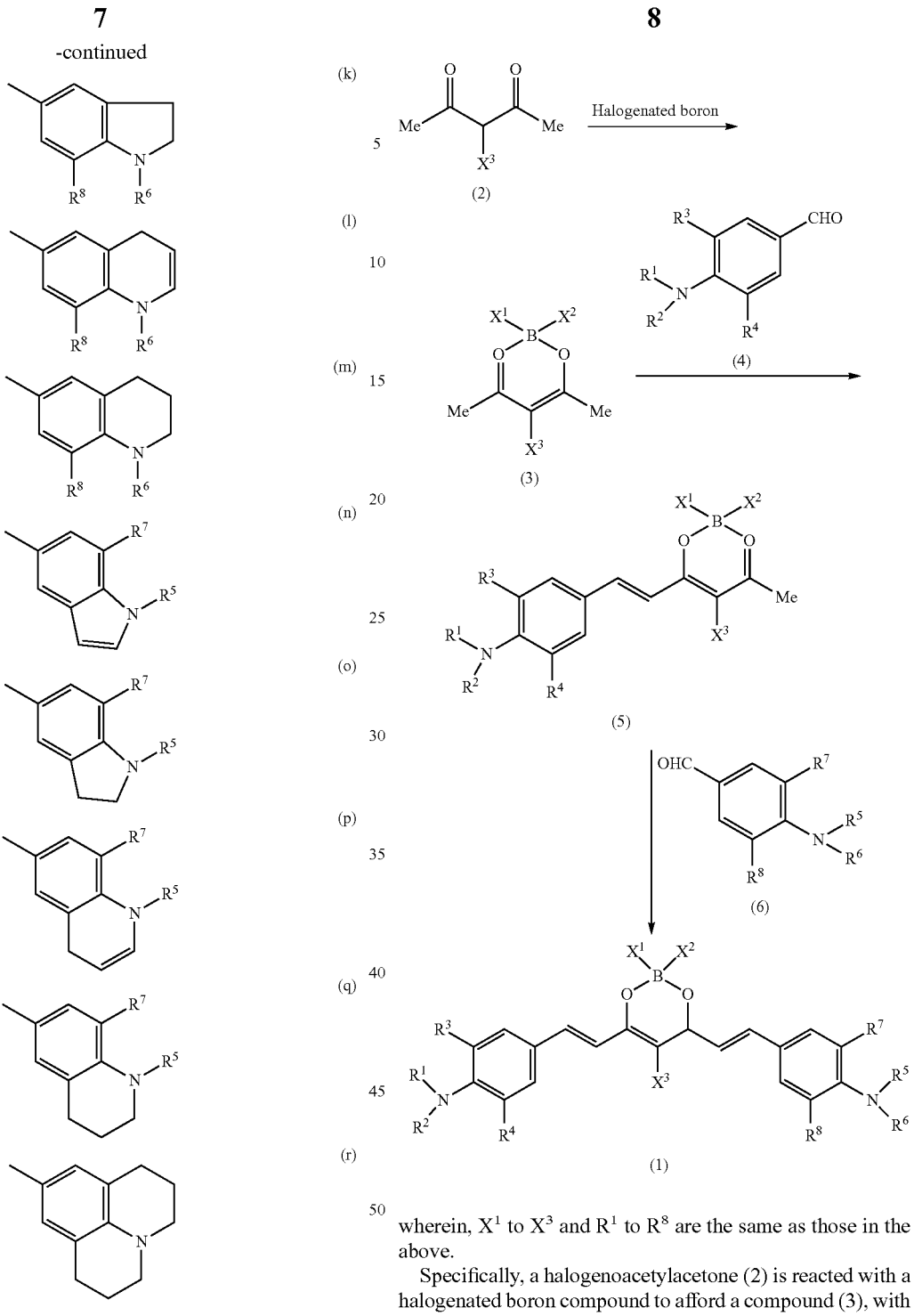

In the structures of (a) to (r), $R^1$ to $R^8$ each represent a group other than the case of forming an alkyl group or an alkenylene group.

Each of m and n represents an integer of 1 to 3, and is preferably 1 or 2, and more preferably 1.

In the case that the inventive compound (1) has an asymmetric carbon atom, optical isomers are present with respect to the inventive compound, and the optical isomers and racemates are all included in the present invention.

The inventive compound (1) can be produced, for example, in accordance with the following reaction formula.

wherein, $X^1$ to $X^3$ and $R^1$ to $R^8$ are the same as those in the above.

Specifically, a halogenoacetylacetone (2) is reacted with a halogenated boron compound to afford a compound (3), with which a benzaldehyde compound (4) is condensed to afford a compound (5), and then the compound (5) and the compound (6) were further condensed together to afford the compound (1).

Examples of the halogenated boron for use in the reaction with the halogenoacetylacetone (2) include $BF_3.Et_2O$, $CF_3BF_3K$, and $CF_3CF_2BF_3K$. The reaction between the halogenoacetylacetone (2) and the halogenated boron can be performed in a polar solvent such as acetonitrile in the presence of an acid such as trimethylsilyl trifluoromethanesulfonate at 0° C. to room temperature.

The condensation reaction between the compound (3) and the benzaldehyde compound (4) is aldol condensation reaction, and can be performed in the presence of a base, for example a borate ester such as trimethoxyborane, triethoxyborane, and tributoxyborane or an amine. The reaction can be performed in an inert solvent such as toluene at a temperature of around room temperature to 80° C.

Through condensation of the obtained compound (5) with the compound (6), the inventive compound (1) is obtained. The condensation reaction between the compound (5) and the compound (6) is also aldol condensation reaction, and can be performed in the same manner as the condensation reaction between the compound (3) and the benzaldehyde compound (4).

In the case that $R^5$ or $R^6$ represents —$(CH_2)_l$—$(Y)_o$—$(CH_2)_p$—Z, the compound (6) can be produced, for example, in accordance with the following reaction formula.

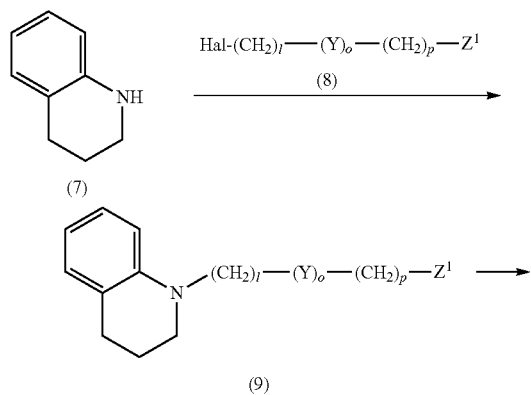

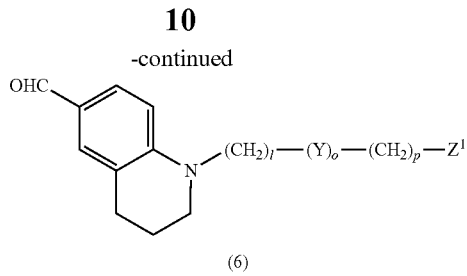

wherein Hal represents a halogen atom; $Z^1$ represents an alkoxycarbonyl group or an alkylsulfonyl group; and Z, Y, l, o, and p are the same as those in the above.

A tetrahydroquinoline (7) is reacted with a compound (8), and the resulting compound (9) is reacted with a formylating agent such as dimethylformamide for hydrolysis to afford a compound (6). Here, the reaction between the tetrahydroquinoline (7) and the compound (8) can be suitably performed in acetonitrile in the presence of a base such as potassium iodide and potassium carbonate at 80 to 100° C. The formylation reaction of the compound (9) can be suitably performed through reaction with dimethylformamide or the like in the presence of an acid catalyst such as phosphorus oxychloride at room temperature. The hydrolysis of the $Z^1$ moiety can be suitably performed through reaction with a base such as sodium hydroxide and potassium hydroxide.

In the case that Y in the above is a heterocycle such as triazole, production can be made in accordance with the following reaction formula.

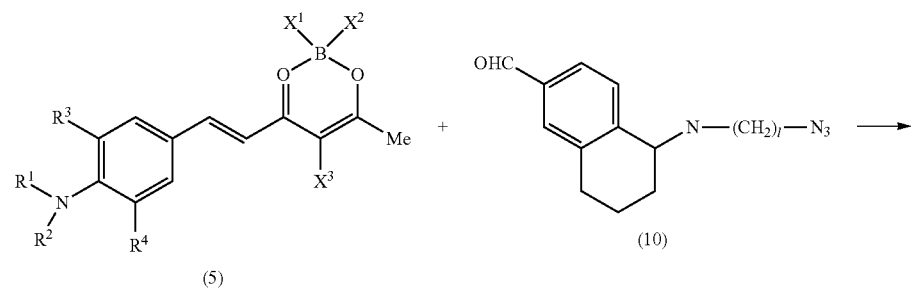

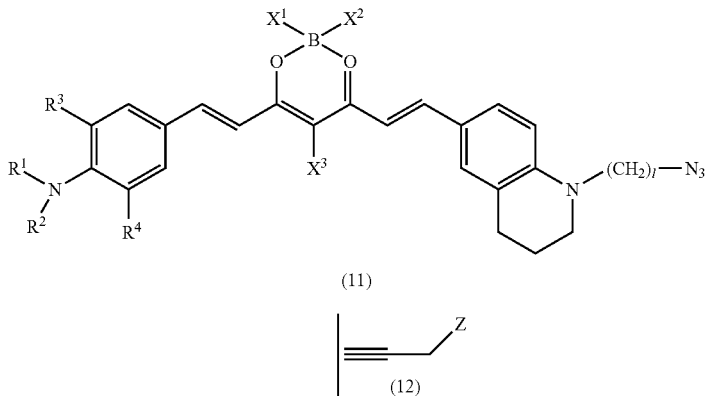

-continued

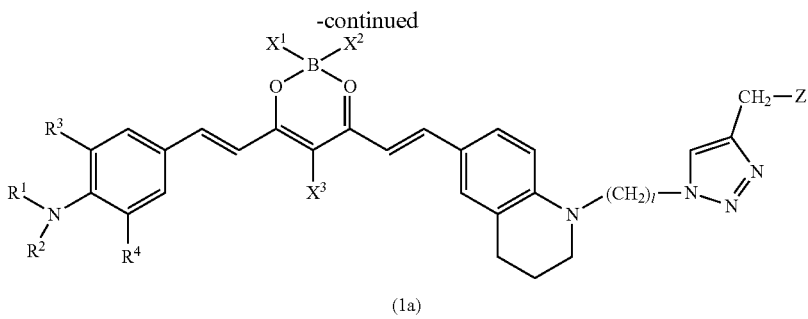

(1a)

wherein $X^1$ to $X^3$, $R^1$ to $R^4$, l, and Z are the same as those in the above.

The compound (5) and a compound (10) are condensed together to afford a compound (11), and the compound (11) is then reacted with a compound (12) to afford a compound (1a).

The condensation reaction between the compound (5) and the compound (10) is aldol condensation reaction, and can be performed in the same manner as the reaction between the compound (3) and the aldehyde compound (4).

The reaction between the compound (11) and the compound (12) is 1,3-dipolar addition reaction of an alkyne and an azide, and smoothly proceeds in a polar solvent such as dimethylformamide and water in the presence of a copper catalyst such as copper sulfate at room temperature.

The inventive compound (1) obtained can be isolated and purified from a reaction mixture by using a common method such as washing, crystallization, recrystallization, and chromatography.

The maximum absorption wavelength of the inventive compound (1) is shifted to the long wavelength side as compared with that of thioflavin T.

When the inventive compound (1) was added to Aβ and the resultant was irradiated with light with a wavelength of 660 nm or longer under physiological conditions, the amount of the native Aβ decreased over time and the amount of oxygenated Aβ with one to four oxygen atoms added thereto increased. The oxygenation efficiency was significantly higher than that of thioflavin T. The oxygenation reaction by the inventive compound (1) is extremely weak for non-amyloidal peptides such as angiotensin IV and methionine enkephalin, and selective for Aβ.

In addition, the oxygenation activity of the inventive compound (1) for highly toxic aggregated Aβ peptide was higher than the oxygenation activity for monomeric Aβ peptide. Moreover, the inventive compound (1) is superior in stability to water and stability under light irradiation.

Accordingly, the inventive compound (1) acts as a catalyst to selectively oxygenate pathogenic amyloids including Aβ peptides, amylin, transthyretin, α-synuclein, tau protein, and huntingtin. When being oxygenated, each of these pathogenic amyloids no longer forms a laminate of β-sheet structures, resulting in loss of pathogenicity. Accordingly, the inventive compound (1) is useful as a preventive/therapeutic drug for a pathogenic amyloid-associated disease including Alzheimer's disease, Parkinson's disease, diabetes mellitus, Huntington's disease, and systemic amyloidosis in animals including humans.

The inventive compound (1) catalyzes oxygenation reaction of pathogenic amyloid. This oxygenation reaction proceeds through excitation of the inventive compound (1) with light followed by oxygenation of amyloid by the excited inventive compound (1). Accordingly, in the case that the inventive compound (1) is used as a pharmaceutical, it is preferable to irradiate a patient with light after administration of the inventive compound (1). Since the wavelength of light to excite the inventive compound (1) is as long as 660 nm or longer, the light is characterized by high tendency to pass through the living body.

Examples of an amino acid residue in amyloid to be oxygenated by the action of the inventive compound (1) include a methionine residue, in which the sulfur atom is oxygenated, and a histidine residue, in which the imidazole ring is oxygenated.

To prepare a pharmaceutical composition containing the inventive compound (1), a formulation suitable for the administration method is selected and the pharmaceutical composition is prepared by using any of various methods for preparing the formulation with a pharmaceutically acceptable carrier. Examples of the dosage form of a pharmaceutical composition containing the inventive compound (1) as a main component include oral formulations such as a tablet, a powder, a granule, a capsule, a liquid, a syrup, an elixir, and an oily or aqueous suspension.

In the case of an injection, a stabilizer, a preservative, or a solubilizing agent is optionally used, and a solution optionally containing any of these adjuvants may be contained in a container and then formulated into a solid formulation through freeze-dying or the like as a formulation to be prepared before use. One dose may be contained in one container, or multiple doses may be contained in one container.

Examples of a formulation for cutaneous application include a liquid, a suspension, an emulsion, an ointment, a gel, a cream, a lotion, a spray, and a patch.

The solid formulation, which contains a pharmaceutically acceptable excipient together with the inventive compound (1), can be formulated, for example, through mixing with a filler, a thickener, a binder, a disintegrator, a solubilizing agent, a wetting agent, a lubricant, or another excipient selected as necessary.

Examples of a liquid formulation include a solution, a suspension, and an emulsion, and a suspending agent, an emulsifier, or another agent is optionally contained as an excipient in a liquid formulation.

In the case that the inventive compound (1) is used as a pharmaceutical for the human body, the dose is in the range of 1 mg to 1 g, and preferably in the range of 1 mg to 300 mg per day for an adult.

EXAMPLES

Hereinafter, the present invention will be specifically described with reference to Examples. However, the scope of the present invention is not limited to the following Examples.

Synthesis Example 1

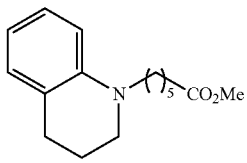

(A)

To potassium iodide (15.9 g, 95.6 mmol) and potassium carbonate (11.0 g, 79.7 mmol) dissolved in acetonitrile (40 mL), 1,2,3,4-tetrahydroquinoline (5.0 mL, 39.8 mmol) and methyl 6-bromohexanoate (7.3 mL, 47.8 mmol) were added at room temperature, and the reaction suspension was stirred in an argon atmosphere at 100° C. for 30 hours. After being cooled to room temperature and filtered, the reaction solution was subjected to concentration under reduced pressure followed by dilution with water and extraction with ethyl acetate. The organic layer was washed with saturated brine and dried over sodium sulfate, and thereafter the organic solvent was removed under reduced pressure. The residue was purified by using flush column chromatography (hexane/EtOAc=100/0 to 80/20) to afford a compound A (7.95 g, 76%).

$^1$H NMR (500 MHz, CDCl$_3$) δ 7.02 (t, J=7.5 Hz, 1H), 6.91 (d, J=7.5 Hz, 1H), 6.51-6.54 (m, 2H), 3.66 (s, 3H), 3.20-3.26 (m, 4H), 2.73 (t, J=6.3 Hz, 2H), 2.31 (t, J=7.5 Hz, 2H), 1.90-1.94 (m, 2H), 1.63-1.69 (m, 2H), 1.56-1.62 (m, 2H), 1.32-1.38 (m, 2H); LRMS (ESI): m/z calcd for [M+H]$^+$: 262; found: 262.

Synthesis Example 2

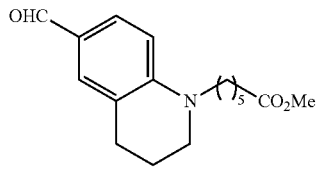

(B)

To the compound A (3.3 g, 12.6 mmol) dissolved in dichloromethane (20 mL), DMF (9.8 mL, 126 mmol) and phosphoryl chloride (3.5 mL, 37.8 mmol) were added, and the mixture solution was stirred in an argon atmosphere at room temperature for 1 day. The reaction mixture solution was diluted with water, neutralized with addition of an aqueous solution of sodium hydroxide, concentrated under reduced pressure, and subjected to extraction with ethyl acetate. The organic layer was washed with saturated brine, and dried over anhydrous sodium sulfate. After the organic solvent was removed under reduced pressure, the resulting residue was dissolved in methanol (20 mL) and 5 N potassium hydroxide (6 mL) was gradually added thereto at 0° C. The reaction mixture solution was stirred at room temperature for 6 hours. After the reaction mixture solution was diluted with water, the pH was adjusted to 1 with addition of an aqueous solution of hydrochloric acid at 0° C., and extraction was then performed with ethyl acetate. The organic layer was washed with saturated brine, and dried over anhydrous sodium sulfate. After the organic solvent was removed under reduced pressure, purification was performed by using silica gel column chromatography (eluent ratio: hexane:ethyl acetate=10:1) to afford a compound B as a pale green solid (2.4 g, 69%).

$^1$H NMR (392 MHz, DMSO-d6) δ 12.03 (s, 1H), 9.56 (s, 1H), 7.48 (d, J=7.2 Hz, 1H), 7.35 (s, 1H), 6.64 (d, J=5.7 Hz, 1H), 3.49-3.18 (m, 4H), 2.83-2.56 (m, 2H), 2.35-2.06 (m, 2H), 1.93-1.66 (m, 2H), 1.63-1.41 (m, 4H), 1.41-1.12 (m, 2H); LRMS (ESI): m/z calcd for [M+H]$^+$: 276; found: 276.

Synthesis Example 3

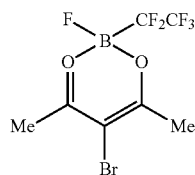

(C)

To a suspension of potassium trifluoro (pentafluoroethyl) borate (CF$_3$CF$_2$BF$_3$K, 0.86 g, 3.8 mmol) in acetonitrile ice-cooled to 0° C., trimethylsilyl trifluoromethanesulfonate (TMS-OTf, 1.03 mL, 5.7 mmol) was added dropwise, and the suspension was stirred at 0° C. for 30 minutes. To this reaction solution, 3-bromopentane-2,4-dione (0.34 g, 1.9 mmol) was added, and the reaction solution was warmed to room temperature and stirred overnight. After the organic solvent was removed under reduced pressure, purification was performed by using flush column chromatography (eluent ratio: hexane:ethyl acetate=90/10 to 70/30) to afford a compound C as a pale yellow crystal (0.33 g, 53%).

Synthesis Example 4

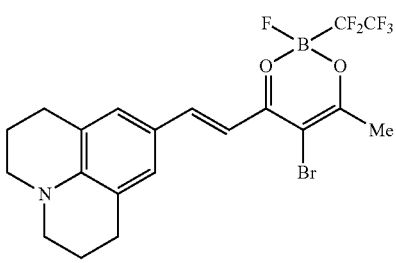

(D)

To a solution of the compound C (163 mg, 0.5 mmol), 9-julolidinecarboxaldehyde (100.7 mg, 0.5 mmol), and normal-butylamine (10 µL, 0.1 mmol) dissolved in toluene (3 mL), tributyl borate (160.5 µL, 0.6 mmol) was added, and the reaction mixture solution was encapsulated under argon. The reaction mixture solution was left to stand at 60° C. for 2 hours, and the reaction solution was cooled to room temperature, and thereafter toluene was removed under reduced pressure, and purification was performed by using flush column chromatography (eluent ratio: hexane:ethyl acetate=90/10 to 70/30) to afford a compound D as a deep purple solid (148 mg, 58%). $^1$H NMR (392 MHz, CDCl$_3$) δ 8.03 (d, J=14.4 Hz, 1H), 7.19 (s, 2H), 6.91 (d, J=14.4 Hz, 1H), 3.45-3.31 (m, 4H), 2.80-2.69 (m, 4H), 2.45 (s, 3H), 1.98 (dd, J=11.2, 5.7 Hz, 4H); LRMS (ESI): m/z calcd for [M+H]$^+$: 510; found: 510.

Synthesis Example 5

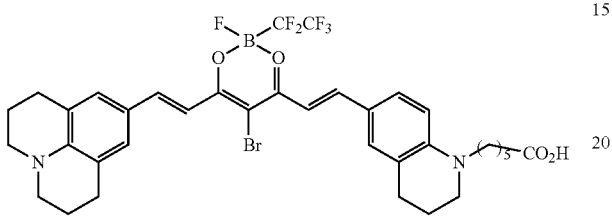

(E)

To a solution of the compound D (15.3 mg, 0.03 mmol), the compound B (16.5 mg, 0.06 mmol), and normal-butylamine (1.2 μL, 0.012 mmol) dissolved in toluene (0.5 mL), tributyl borate (80 μL, 0.3 mmol) was added, and the reaction mixture solution was encapsulated under argon. The reaction mixture solution was left to stand at 70° C. for 12 hours, and the reaction solution was cooled to room temperature, and thereafter toluene was removed under reduced pressure, and purification was performed by using HPLC (MeCN/0.1% TFA=10/90 to 100/0) to afford a compound E as a deep purple solid (15.8 mg, 69%).

$^1$H NMR (392 MHz, DMSO-d6) δ 7.66 (dd, J=14.5, 9.1 Hz, 2H), 7.46 (d, J=8.9 Hz, 1H), 7.41 (s, 1H), 7.30 (s, 2H), 7.01 (dd, J=17.4, 14.6 Hz, 2H), 6.69 (d, J=9.0 Hz, 1H), 3.45-3.30 (m, 8H), 2.75-2.67 (m, 6H), 2.22 (t, J=7.3 Hz, 2H), 1.92-1.78 (m, 6H), 1.52 (dd, J=15.1, 7.4 Hz, 4H), 1.32 (dd, J=15.1, 8.1 Hz, 2H); LRMS (ESI): m/z calcd for [M+H]$^+$: 767; found: 767.

Synthesis Example 6

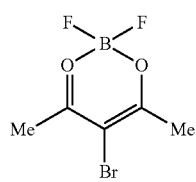

(F)

A solution containing 3-bromopentane-2,4-dione (0.9 g, 5 mmol) and a diethyl ether complex of boron trifluoride (BF$_3$.Et$_2$O, 0.94 mL, 7.5 mmol) in acetonitrile was stirred at 0° C. in an argon atmosphere. Concentration under reduced pressure was performed, and the residue was purified by using flush column chromatography (eluent ratio: hexane: ethyl acetate=90/10 to 60/40) to afford a compound F as a pale yellow solid (0.48 g, 42%).

Synthesis Example 7

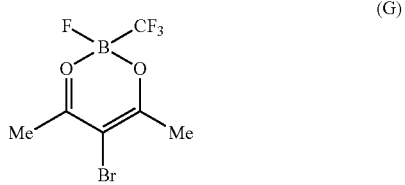

(G)

A compound G was synthesized with 3-bromopentane-2, 4-dione and potassium trifluoro(trifluoromethyl)borate (CF$_3$BF$_3$K) in the same manner as for the compound C. A pale brown oily substance (0.85 g, 62%).

Synthesis Example 8

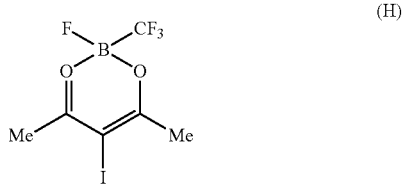

(H)

A compound H was synthesized with 3-iodopentane-2,4-dione and potassium trifluoro(trifluoromethyl)borate (CF$_3$BF$_3$K) in the same manner as for the compound C. A pale brown oily substance (0.34 g, 51%).

Synthesis Example 9

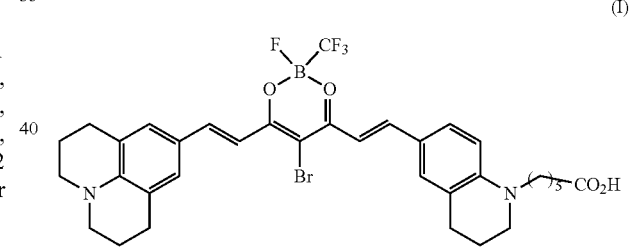

(I)

A compound I was synthesized with the compound G and 9-julolidinecarboxaldehyde in the same manner as for the compound E. A deep blue solid (45% in two steps). LRMS (ESI): m/z calcd for [M+H]$^+$: 717; found: 717.

Synthesis Example 10

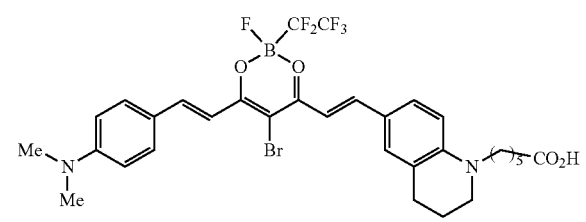

(J)

A compound J was synthesized with the compound C and 4-dimethylaminobenzaldehyde in the same manner as for the compound E. A deep blue solid (8% in two steps) LRMS (ESI): m/z calcd for [M+H]: 715; found: 715.

Synthesis Example 11

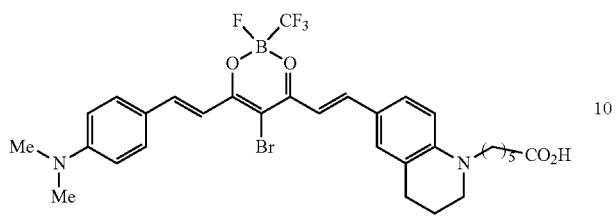
(K)

A compound K was synthesized with the compound G and 4-dimethylaminobenzaldehyde in the same manner as for the compound E. A deep blue solid (15% in two steps). LRMS (ESI): m/z calcd for [M+H]$^+$: 665; found: 665.

Synthesis Example 12

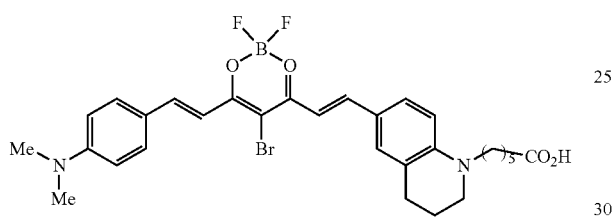
(L)

A compound L was synthesized with the compound F and 4-dimethylaminobenzaldehyde in the same manner as for the compound E. A deep blue solid (8% in two steps). LRMS (ESI): m/z calcd for [M+H]$^+$: 615; found: 615.

Synthesis Example 13

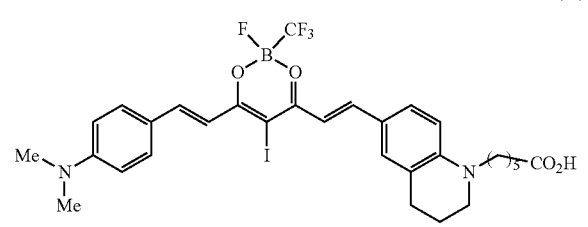
(M)

A compound M was synthesized with the compound H and 4-dimethylaminobenzaldehyde in the same manner as for the compound E. A deep blue solid (13% in two steps). LRMS (ESI): m/z calcd for [M+H]$^+$: 713; found: 713.

Synthesis Example 14

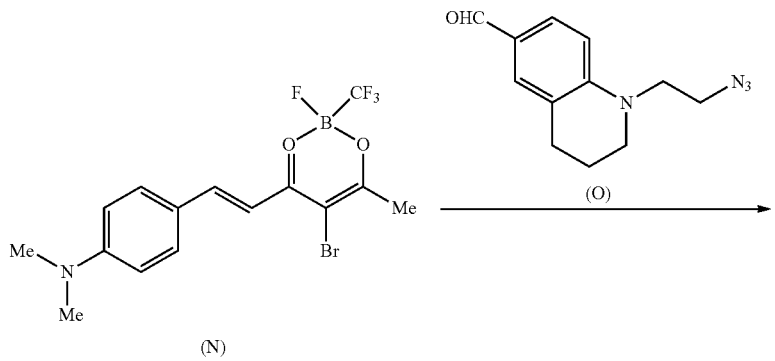
(N)  (O)

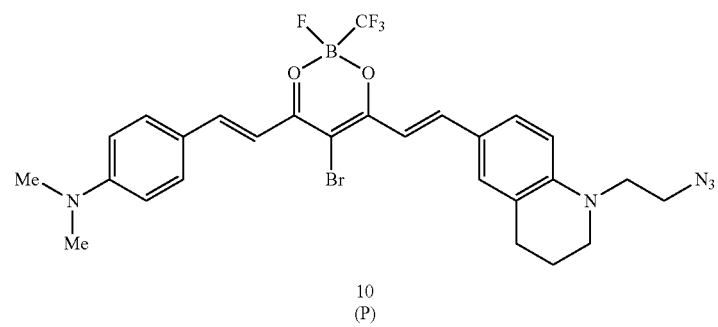
(P)

A compound N was synthesized with the compound G and 4-dimethylaminobenzaldehyde in the same manner as for the compound D. Thereafter, a compound P was synthesized with the compound N and a compound O in the same manner as for the compound E. A deep blue solid (24% in two steps).

LRMS (ESI): m/z calcd for [M+H]$^+$: 620; found: 620.

Synthesis Example 15

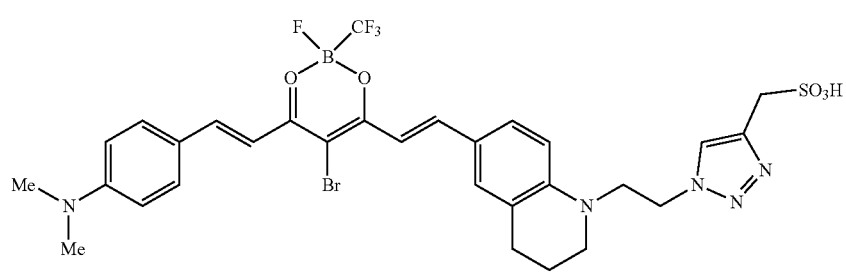

To a solution of the compound P (5.0 mg, 8 µmol) and sodium 2-propyne-1-sulfonate in a mixture of ethanol (0.4 mL) and DMF (0.4 mL), $CuSO_4$-5$H_2O$ (1.0 mg, 4 µmol) and L-ascorbic acid (7.0 mg, 40 µmol) in DMF (0.3 mL) and $H_2O$ (0.1 mL) were added, and the reaction mixture solution was stirred at room temperature for 8 hours. Thereafter, the reaction mixture solution was freeze-dried, and then purified by using HPLC (MeCN/0.1% TFA=10/90 to 100/0) to afford a compound Q. A deep purple solid (1.6 mg, 27%).

LRMS (ESI): m/z calcd for [M+H]$^+$: 740; found: 740.

Synthesis Example 16

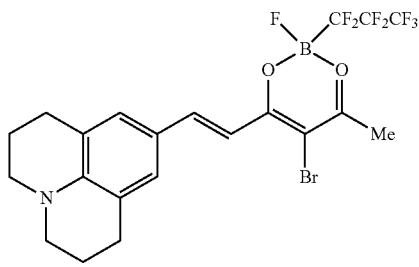

An intermediate compound was obtained as a pale brown oil (79.0 mg, 21%) by using the method in Synthesis Example 3 with potassium trifluoro(heptafluoropropyl)borate (276.0 mg, 1.0 mmol) in place of potassium trifluoro (pentafluoroethyl)borate.

A compound R was obtained as a deep purple solid (20.7 mg, 37%) by using the method in Synthesis Example 4 with the intermediate compound (37.7 mg, 0.1 mmol) in place of the compound C.

$^1$H NMR (400 MHz, $CDCl_3$) δ 8.02 (d, J=14.4 Hz, 1H), 7.18 (s, 2H), 6.90 (d, J=14.4 Hz, 1H), 3.58-3.33 (m, 4H), 2.88-2.72 (m, 4H), 2.44 (s, 3H), 2.10-1.90 (m, 4H); 13C NMR (125 MHz, $CDCl_3$) δ 179.74, 174.17, 154.78, 149.42, 132.10, 121.82, 121.64, 108.49, 95.58, 50.55, 27.41, 24.68, 20.90; $^{19}$F NMR (369 MHz, $CDCl_3$) δ −81.48 (3F), −128.32 (2F), −135.96 (2F), −152.51 (1F); 11B NMR (126 MHz, $CDCl_3$) δ 1.07 (s); LRMS (ESI): m/z calcd for [M+H]$^+$ 560.1, found 560.1.

Synthesis Example 17

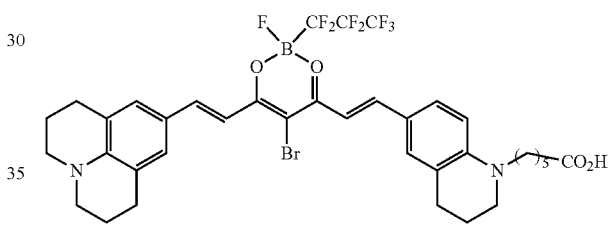

A compound S was obtained as a deep blue solid (20.8 mg, 85%) by using the method in Synthesis Example 5 with the compound R (16.8 mg, 0.03 mmol) and the compound B (16.5 mg, 0.04 mmol) in place of the compound D and the compound A, respectively.

$^1$H NMR (500 MHz, DMSO-d6) δ 7.63 (d, J=14.7 Hz, 1H), 7.60 (d, J=14.7 Hz, 1H), 7.39 (d, J=9.0 Hz, 1H), 7.34 (s, 1H), 7.22 (s, 2H), 6.95 (d, J=14.7 Hz, 1H), 6.91 (d, J=14.7 Hz, 1H), 6.62 (d, J=9.0 Hz, 1H), 3.74-3.12 (m, 8H), 2.94-2.56 (m, 6H), 2.17 (t, J=7.3 Hz, 2H), 2.03-1.69 (m, 6H), 1.63-1.39 (m, 4H), 1.39-1.19 (m, 2H); $^{13}$C NMR (125 MHz, DMSO-d6) δ 174.41, 169.03, 168.39, 149.74, 149.05, 148.40, 147.74, 132.38, 130.69, 122.84, 121.79, 121.43, 121.12, 110.94, 110.78, 109.57, 94.61, 50.60, 49.84, 49.35, 33.61, 27.16, 26.75, 25.93, 25.85, 24.34, 20.90, 20.51; $^{19}$F NMR (369 MHz, DMSO-d6) δ −81.38 (3F), −128.29 (2F), −135.73 (2F), −154.02 (1F); $^{11}$B NMR (126 MHz, DMSO-d6) δ −1.22 (s); LRMS (ESI): m/z calcd for [M+H]$^+$ 817.2, found 817.2.

Test Example 1

An in vitro oxygenation experiment using Aβ$_{1-42}$ as a substrate was conducted to confirm that each of the inventive compounds actually have Aβ oxygenation activity. A test compound (1 µM in each case) was added to phosphate buffer (pH 7.4)/cell culture solution (containing 0.1% horse serum) (1:3) containing Aβ$_{1-42}$ (10 µM), and incubated under LED irradiation (wavelength: 660 nm, 730 nm) at 37°

C., and then the reaction was tracked by using a mass spectrometer (MALDI-TOF MS). The native $A\beta_{1-42}$ and the $Na^+$ adduct were mainly observed before light irradiation. After light irradiation, an ion peak indicating the presence of the oxygenated form was observed over time (FIG. 1, FIG. 2).

Eventually, oxygenation of the Aβ proceeded under light irradiation at both of 660 nm and 730 nm for the compound E and the compound I (FIG. 1); and oxygenation of the Aβ proceeded under light irradiation at 730 nm for the compound K and the compound M (FIG. 2).

Test Example 2

A culture medium for rat adrenal medulla-derived pheochromocytoma PC 12 cells (purchased from RIKEN, Japan) seeded on a poly-D-lysine-coated 96-well plate was replaced with 75 μL of a Dulbecco's modified Eagle's medium containing 0.1% horse serum, and the culture was incubated in a 5% $CO_2$ atmosphere at 37° C. for 1 day, and 25 μL of a phosphate buffer saline (pH 7.4) containing a inventive compound was then added thereto. Thereafter, the mixed solution was incubated under LED irradiation (wavelength: 660 nm, 10 mW) (without light irradiation for dark) at 37° C. for 5 minutes. Further, the cell culture plate containing the reaction solution was incubated in a 5% $CO_2$ atmosphere at 37° C. for 48 hours. Finally, the Cell Count Reagent SF (10 μL: purchased from NACALAI TESQUE, INC.) containing WST-8 was added, and the culture was incubated in a 5% $CO_2$ atmosphere at 37° C. for 3 hours, and thereafter the cell viability was determined from the absorbance at 450 nm (reference wavelength: 655 nm).

From the results shown in FIG. 3, it was found that toxicity under light irradiation was the lowest for the compound E, and higher in the order of the compound J, the compound K, and the compound L. These results suggest that toxicity is the highest in the case that the boron center is $BF_2$, and lower in the order of $BFCF_3 > BFC_2F_5$. The result of comparison between the compound J and the compound E suggests that conversion of N,N-dimethylaniline into julolidine provides reduced toxicity.

The result of comparison between the compound K and the compound M, although not illustrated, suggests that iodine provides more reduced toxicity than in the case of bromine.

Test Example 3

A phosphate buffer saline (pH 7.4) containing Aβ (40 μM) was incubated at 37° C. for 3 hours. Subsequently, the compound E was added thereto (4 or 12 μM). A culture medium for rat adrenal medulla-derived pheochromocytoma PC 12 cells (purchased from RIKEN, Japan) seeded on a poly-D-lysine-coated 96-well plate was replaced with 75 μL of a Dulbecco's modified Eagle's medium containing 0.1% horse serum, and the culture was incubated in a 5% $CO_2$ atmosphere at 37° C. for 1 day, and 25 μL of the phosphate buffer saline (pH 7.4) containing Aβ and the compound E was then added thereto (final volume: 100 μL, final concentration of Aβ: 10 μM, final concentration of compound E: 1 or 3 μM). Thereafter, the mixed solution was incubated under LED irradiation (wavelength: 660 nm, 10 mW) (without light irradiation for dark) at 37° C. for 5 minutes. Further, the cell culture plate containing the reaction solution was incubated in a 5% $CO_2$ atmosphere at 37° C. for 48 hours. Finally, the Cell Count Reagent SF (10 μL: purchased from NACALAI TESQUE, INC.) containing WST-8 was added, and the culture was incubated in a 5% $CO_2$ atmosphere at 37° C. for 3 hours, and thereafter the cell viability was determined from the absorbance at 450 nm (reference wavelength: 655 nm).

From the results shown in FIG. 4, an attempt was made to examine whether the toxicity of $A\beta_{1-42}$ can be reduced through oxygenation of the $A\beta_{1-42}$ in the presence of cells. The rat adrenal medulla-derived neural model cells PC12 were used for the cells, and the compound E was used as a catalyst. The cell viability was determined through measurement of the absorption by WST-8 at 450 nm by using a plate reader. While significant cell death was found for the case of addition of $A\beta_{1-42}$ and the compound E without light irradiation, as with the case of addition only of $A\beta_{1-42}$, the cell viability was significantly improved under light irradiation. These results suggest that the cytotoxicity was reduced through selective oxygenation of $A\beta_{1-42}$ by the catalyst.

Test Example 4

The compound K (2 μM) was added to glycerol/water (0:100, 10:90, 30:70, 50:50) dissolving benzoylmethionine (2000 μM) therein, and the resultant was subjected to LED irradiation (wavelength: 730 nm) at room temperature, and thereafter the reaction was tracked by using LC/MS (ESI-Q).

From the results shown in FIG. 5, the benzoylmethionine/oxygenated form ratio (%) was found to be higher as the concentration of glycerol, which has high viscosity, was higher. These results suggest that the oxygenation activity was developed through suppression of the intramolecular rotational motion of the compound K accompanied by production of singlet oxygen.

Test Example 5

A neutral phosphate buffer containing a catalyst was incubated without light irradiation or under light irradiation (660 nm), and thereafter ethanol containing benzyl alcohol (as an internal standard) was added thereto, and analysis was performed by using HPLC.

Any catalyst without light irradiation was stable after 1 day.

As shown in FIG. 6, under light irradiation, it was found that stability was the lowest for the case that the boron center was $BF_2$ (compound L), and higher in the order of $BFCF_3$ (compound K)<$BFCF_2CF_3$ (compound J); and that stability was higher for the compounds including julolidine at the donor site (compound E, compound I) than those of the corresponding dimethylaniline forms (compound K, compound J).

Test Example 6: Oxygenation Reaction in Mouse Brain Extract

The brain excised from an eight-month-old App knock-in ($App^{NL-C-F/NL-C-F}$) mouse (Alzheimer's model mouse) was separated into the cerebral cortex, the hippocampus, and the residual brain tissues. The cerebral cortex and the hippocampus were homogenized together in a phosphate buffer saline, and the suspension was stored at −80° C. The compound E or riboflavin was added to the suspension of the lysate to a final concentration of 100 μM or 50 μM, and the resultant was subjected to light irradiation (at a wavelength of 780 nm), or stored in dark at room temperature. At an arbitrary point of time, an arbitrary aliquot of the reaction mixture was diluted with formic acid to a final concentration of 70%, concentrated, and redissolved in a 6 M aqueous solution of urea. An internal standard (Aβ$_{1-40}$, PEPTIDE INSTITUTE, INC., Japan) was added, and the residual mixture was treated with a ZipTip, and Arctic Aβ$_{1-38}$ and Aβ$_{1-42}$ were analyzed by using a MALDI-TOF MS.

The MALDI-TOF MS analysis confirmed the conversion of each Aβ peptide from decrease of the peak intensity. The peak intensity decreased by 36%/53%/74% for Arctic Aβ$_{1-38}$, and by 43%/60%/83% for Arctic Aβ$_{1-42}$ 30 minutes, 60 minutes, and 150 minutes after the reaction (FIG. 7).

A control experiment carried out in a dark room demonstrated that light irradiation is important for decrease of the amount of each Aβ peptide.

When Aβ$_{1-38}$ and Aβ$_{1-42}$ were converted by compound E at a yield of 53% and 60%, respectively (after a lapse of 60 minutes), peptides A, B, and C (peptides with molecular weights of 3770, 4286, and 4968, respectively), which are non-Aβ endogenous substances and each have mass spectral values similar to those for Aβ, were not converted when compared with those at min 0 (FIG. 8).

When riboflavin was used, in contrast, not only Aβ$_{1-38}$ and Aβ$_{1-42}$ but also peptide A, peptide B, and peptide C, which are non-Aβ peptides, were consumed to a significant degree (FIG. 9). These results indicate that the compound E selectively oxygenates Aβ peptides even in a brain lysate having a low Aβ concentration and containing a large amount of non-target molecules.

Test Example 7: Oxygenation Under Mouse Skin

To demonstrate the usefulness of the compound E for oxygenation of amyloid proteins in the living body, reaction under the mouse skin (a therapeutic model for peripheral amyloid diseases) was examined. A microtube containing a phosphate buffer containing Aβ$_{1-42}$ (20 μM, aggregated in advance for 3 hours) and the compound E or a compound 3 [9-(6-bromo-3-methyl-1,3-benzotriazol-3-ium-2-yl)-julolidine] was implanted in the back skin of a wild mouse, and light irradiation with an LED lamp was performed from the outside of the mouse body at a wavelength of 780 nm for 30 minutes (FIG. 10). As a control experiment, another microtube containing the same components (Aβ$_{1-42}$ (20 μM, aggregated in advance for 3 hours) and the compound E or the compound 3) was directly subjected to light irradiation outside of the mouse body. The reaction mixture was analyzed by using a MALDI-TOF MS, and then subjected to ZipTip treatment for analysis. The percentage of oxygenation ratio was calculated from the percentage of oxygenation ratio under the skin and the oxygenation ratio outside of the skin "[oxygenation ratio under mouse skin/oxygenation ratio outside of mouse skin]×100".

As shown in FIG. 11, the percentage of oxygenation ratios (the oxygenation rate in the living body relative to the oxygenation rate outside of the body) with the compound E was 65%, and, on the other hand, the percentage of oxygenation ratios with the compound 3 (10 μM) was 12%. The difference between the results for the compound E and the compound 3 lies in the difference in light intensity after passing through the skin. These results indicate that the compound E as an oxygenation catalyst capable of being activated by NIR light is suitable for oxygenation of toxic aggregated amyloid proteins in the living body.

Test Example 8: Conversion of Furfuryl Alcohol or N-Benzoyl-Met Under Different Glycerol Concentrations To a glycerol-methanol mixed solvent (glycerol: 0, 10, 30, or 50%), furfuryl alcohol or N-benzoyl-Met (2 mM in each case) and the compound E (2 μM) were added, and the mixture was subjected to light irradiation (wavelength: 780 nm) at room temperature, and the concentration of furfuryl alcohol or N-benzoyl-Met was quantified by using a UV absorptiometer with LC/MS 10 minutes, 20 minutes, and 30 minutes after the initiation of light irradiation.

FIGS. 12 and 13 show the results. The oxygenation reaction rate of furfuryl alcohol (specifically reacts with $^1O_2$), the reaction catalyzed by the compound E, was higher as the viscosity of the solvent was higher. Oxygenation of N-benzoyl-Met catalyzed by the compound E similarly accelerated as the viscosity of the solvent was higher. These observation results suggest that the compound E provided with a prolonged life time of activated state through inhibition of the free rotation of the single bond between the donor and the acceptor provides a higher quantum yield of $^1O_2$.

Test Example 9: Aβ Selectivity of Oxygenation

A phosphate buffer (pH 7.4) containing an Aβ peptide before aggregation (prepared through incubation at 37° C. for 1 hour), angiotensin-IV (AT4), Met-enkephalin (ME), or somatostatin (Sst) (20 μM in each case) was subjected to light irradiation at 37° C. for 30 minutes in the presence of the compound E (5 μM) at 780 nm (7 mW) or in the presence of riboflavin (5 μM) at 500 nm.

The compound E (25 mol %) oxygenated 44% of the pre-aggregated Aβ peptide (FIG. 14). The oxygenation rate was lower than 5% for the peptides other than the Aβ peptide, in spite of the same reaction conditions. Riboflavin, which is a catalyst having no cognitive function for cross-β-sheets, is non-selective, and the yield of oxygenated Aβ (43%) was almost comparable to the yields obtained by using the non-target substrates (angiotensin-IV: 35%, Met-enkephalin: 50%, somatostatin: 60%). This target selectivity is important for selective oxygenation of aggregated Aβ in a brain lysate in the presence of cells.

Test Example 10: Comparison of Oxygenation Activity for Aβ$_{1-42}$ and Toxicity Among Photocatalysts (1) Oxygenation Aβ$_{1-42}$ isopeptide (concentration: 250 μM in 0.1% aqueous solution of trifluoroacetic acid), angiotensin IV (200 μM aqueous solution), Met-enkephalin (200 μM aqueous solution), and somatostatin (200 μM aqueous solution) were added to a phosphate buffer or phosphate buffer saline (pH 7.4) (with 0.1 M aqueous solution of sodium hydroxide, as necessary) so that a final peptide concentration of 20 μM or 40 μM (pH 7.4) was reached. Before being subjected to oxygenation reaction, the Aβ$_{1-42}$ solution was incubated at 37° C. for 1 to 3 hours. The phosphate buffer containing 40 μM of Aβ was diluted with a Dulbecco's modified Eagle's medium (DMEM, Life Technologies) containing 0.1% horse serum and buffered with 25 mM of 4-(2-hydroxyethyl)-1-piperazineethanesulfonic acid (HEPES).

To each solution, 5 to 10 (200 μM dimethyl sulfoxide solution) of riboflavin (1 mM in 0.1% aqueous solution of trifluoroacetic acid/acetonitrile (1:1)), the compound 3 (1 mM in acetonitrile), CRANAD-2 ((T-4)-[(1E,6E)-1,7-bis[4-(dimethylamino)phenyl]-1,6-heptadiene-3,5-dionato-κO$^3$, κO$^5$]difluoroboron) (200 μM dimethyl sulfoxide solution) or the compound E, the compound I, the compound J, the compound L, the compound K, or the compound S was added. Solutions of the compounds with a final concentration of 2 µM were used for evaluation of oxygenation of $A\beta_{1-42}$. Solutions of the compounds with a final concentration of 5 µM were used for evaluation of peptide selectivity. Each mixture was subjected to light irradiation with an LED (wavelength: 500, 660, or 780 nm) at a distance of approximately 5 to 10 cm at room temperature. A control group without light irradiation was additionally prepared. Reaction was analyzed through monitor analysis with a MALDI-TOF MS. Degree of oxygenation was determined as a ratio: degree of oxygenation (%)=(total of MS intensities for n[O] adducts)/(MS intensity for native+total of MS intensities for n[O] adducts)×100. Aliquots of each reaction solution were desalted with a ZipTip U-C18 (Merck Millipore), as necessary, before mass spectrometry. Tables 1 and 2 below show the results.

(2) Cell Assay

Rat pheochromocytoma PC 12 cells were suspended with DMEM containing 5% horse serum and 10% fetal bovine serum, seeded in a poly-D-lysine-coated 96-well plate at a concentration of 10,000 cells per well, and incubated in a 5% carbon dioxide atmosphere at 37° C. for 3 days. After the solvent was removed, the cells were washed with 150 µL of serum-free DMEM, and DMEM (75 µL) containing 0.1% horse serum was added thereto. Thereafter, the 96-well plate was incubated in a 5% carbon dioxide atmosphere at 37° C. for 1 day for use in oxygenation reaction. In oxygenation reaction, the compound E (100 µM dimethyl sulfoxide solution) was added to a phosphate buffer saline containing Aβ (aggregated in advance for 3 hours, 40 µM) and 25 µL of the above cell solution (final concentration of Aβ: 10 µM, final concentration of compound E: 1 µM). The mixture was irradiated with an LED (wavelength: 780 nm) at a distance of approximately 5 cm at 37° C. for 5 minutes. The cells were incubated in a 5% carbon dioxide atmosphere at 37° C. for 48 hours. The cell viability was measured by using the Cell Count Reagent SF (NACALAI TESQUE, INC., Kyoto, Japan) with WST-8 (2-(2-methoxy-4-nitrophenyl)-3-(4-nitrophenyl)-5-(2,4-disulfophenyl)-2H-tetrazolium). Tables 1 and 2 below show the results.

TABLE 1

| | | a | Degree of | b | |
|---|---|---|---|---|---|
| No. | Photocatalyst | Maximum wavelength $\lambda_{max}$ (nm) | oxygenation (%) of Aβ42 (λ = 660 nm) | $LC_{50}$ (dark) (µM) | $LC_{50}$ (light) (µM) |
| 1 | Compound 3 | 456 | trace | — | — |
| 2 | CRANAD-2 | 579 | trace | — | — |
| 3 | Compound L (Synthesis Example 12) | 623 | 73 | 6.27 ± 1.79 | 0.024 ± 0.004 |
| 4 | Compound K (Synthesis Example 11) | 620 | 86 | 1.89 ± 0.28 | 0.143 ± 0.035 |
| 5 | Compound J (Synthesis Example 10) | 622 | 79 | 3.65 ± 0.35 | 1.49 ± 0.59 c | a: A phosphate buffer (pH 7.4) solution containing pre-aggregated $A\beta_{1-42}$ (20 µM, incubated at 37° C. for 3 hours) and a catalyst (2 µM) was subjected to light irradiation (wavelength: 660 nm) at 37° C. for 30 minutes. Thereafter, the reaction mixture was analyzed by using a MALDI-TOF MS.

b: $LC_{50}$ (dark) indicates the toxicity of a compound itself, and $LC_{50}$ (light) indicates the phototoxicity of a compound. The PC 12 cells were placed in dark or subjected to photocatalytic treatment under light irradiation (wavelength: 660 nm), and incubated at 37° C. for 5 minutes, and then in a 5% carbon dioxide atmosphere at 37° C. for 48 hours, for which the cell viability was analyzed (n=5, mean±SEM).

c: A significant difference from the compound L and compound K was found for the compound J under light irradiation with p<0.05 (Tukey test).

TABLE 2

| | | a | Degree of | b | |
|---|---|---|---|---|---|
| No. | Photocatalyst | Maximum wavelength $\lambda_{max}$ (nm) | oxygenation (%) of Aβ42 (λ = 780 nm) | $LC_{50}$ (dark) (µM) | $LC_{50}$ (light) (µM) |
| 1 | Compound J (Synthesis Example 10) | 620 | 41 | 3.90 ± 1.34 | 2.91 ± 0.47 |
| 2 | Compound I (Synthesis Example 9) | 645 | 52 | >10 | 1.67 ± 0.19 |
| 3 | Compound E (Synthesis Example 5) | 639 | 58 | >10 | >10 |
| 4 | Compound S (Synthesis Example 17) | 633 | 37 | >10 | >10 | a: A phosphate buffer (pH 7.4) containing pre-aggregated $A\beta_{1-42}$ (20 µM, obtained through incubation at 37° C. for 3 hours) and a catalyst (2 µM) were subjected to light irradiation at 780 nm (14 mW) at 37° C. for 30 minutes. The reaction mixture was analyzed by using a MALDI-TOF MS.

b: The PC 12 cells were treated together with a photocatalyst (1 µM) at 37° C. for 5 minutes in dark or under light irradiation (wavelength: 780 nm), and thereafter the cell viability was analyzed (n=3, mean±SEM).

The invention claimed is:

1. A curcumin-boron complex represented by the following formula (1) or a salt thereof:

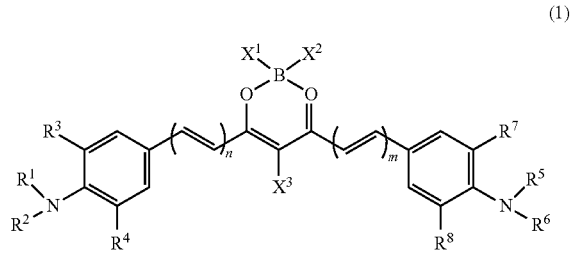

(1)

wherein

X¹ and X² are identical or different, and each represent a halogenoalkyl group or a halogen atom;

X³ represents a bromine atom, an iodine atom, or a selenium atom;

R¹ and R² are identical or different, and each represent a hydrogen atom or an optionally substituted alkyl group;

R³ and R⁴ are identical or different, and each represent a hydrogen atom, a halogen atom, an alkoxy group, or an optionally substituted alkyl group, or R¹ and R³ or R² and R⁴ are optionally taken together to form an optionally substituted alkylene group or alkenylene group;

R⁵ and R⁶ are identical or different, and each represent a hydrogen atom or an optionally substituted alkyl group;

$R^7$ and $R^8$ are identical or different, and each represent a hydrogen atom, a halogen atom, an alkoxy group, or an optionally substituted alkyl group, or $R^5$ and $R^7$ or $R^6$ and $R^8$ are optionally taken together to form an optionally substituted alkylene group or alkenylene group; and m and n each represent an integer of 1 to 3.

2. The curcumin-boron complex or salt thereof according to claim 1, wherein $X^1$ is a halogenoalkyl group, and $X^2$ is a halogen atom.

3. The curcumin-boron complex or salt thereof according to claim 1, wherein m and n are each 1.

4. The curcumin-boron complex or salt thereof according to claim 1, wherein the optionally substituted alkyl group represented by any of $R^1$, $R^2$, $R^3$, $R^4$, $R^5$, $R^6$, $R^7$, and $R^8$ is an alkyl group optionally having one or more substituents selected from the group consisting of a carboxy group, a sulfonic acid group, a hydroxy group, an amino group, —CO—, —CONH—, and a triazole group.

5. The curcumin-boron complex or salt thereof according to claim 1, wherein the alkylene group or alkenylene group formed by $R^1$ and $R^3$, $R^2$ and $R^4$, $R^5$ and $R^7$, or $R^6$ and $R^8$ taken together has two or three carbon atoms.

6. A pharmaceutical comprising the curcumin-boron complex or salt thereof according to claim 1 as an active ingredient.

7. The pharmaceutical according to claim 6, wherein the pharmaceutical is a therapeutic drug for Alzheimer's disease.

8. A pharmaceutical composition comprising the curcumin-boron complex or salt thereof according to claim 1 and a pharmaceutically acceptable carrier.

9. A method for treating Alzheimer's disease, the method comprising administering an effective amount of the curcumin-boron complex or salt thereof according to claim 1 to a subject in need thereof.

* * * * *